United States Patent [19]

Krämer et al.

[11] Patent Number: 5,128,368
[45] Date of Patent: Jul. 7, 1992

[54] PESTICIDES BASED ON SUBSTITUTED AMINOMETHYL HETEROCYCLIC COMPOUNDS

[75] Inventors: Wolfgang Krämer, Burscheid; Joachim Weissmüller, Monheim; Graham Holmwood; Dieter Berg, both of Wuppertal; Stefan Dutzmann, Duesseldorf; Wilhelm Brandes, Leichlingen; Gerd Hänssler; Paul Reinecke, both of Leverkusen, all of Fed. Rep. of Germany

[73] Assignee: Bayer Aktiengesellschaft, Leverkusen, Fed. Rep. of Germany

[21] Appl. No.: 595,143

[22] Filed: Oct. 10, 1990

Related U.S. Application Data

[60] Division of Ser. No. 423,607, Oct. 17, 1989, Pat. No. 4,988,729, which is a continuation of Ser. No. 184,865, Apr. 22, 1988, abandoned.

[30] Foreign Application Priority Data

May 8, 1987 [DE] Fed. Rep. of Germany ....... 3715482

[51] Int. Cl.$^5$ .................. A61K 31/335; C07D 407/12; C07D 317/10
[52] U.S. Cl. .................................... 514/452; 514/467; 549/370; 549/414; 549/448; 549/451
[58] Field of Search ............... 549/370, 414, 448, 451; 514/452, 467

[56] References Cited

U.S. PATENT DOCUMENTS

| | | | |
|---|---|---|---|
| 2,513,747 | 7/1950 | Sallmann et al. | 549/451 |
| 2,606,909 | 8/1952 | Blicke | 549/451 |
| 4,503,059 | 3/1985 | Krämer et al. | 549/451 |
| 4,668,700 | 5/1987 | Kramer et al. | 549/451 |

FOREIGN PATENT DOCUMENTS

| | | |
|---|---|---|
| 0097822 | 5/1983 | European Pat. Off. |
| 0131793 | 6/1984 | European Pat. Off. |
| 0158922 | 4/1985 | European Pat. Off. |
| 644855 | 8/1984 | Switzerland |
| 1031916 | 6/1966 | United Kingdom |

OTHER PUBLICATIONS

Size of muscarinic receptor anionic binding site related to onium group of ligands with a 1,3-oxathiolane nucleus Tetrahedron Letters No. 15, pp. 1309-1212, 1977, Printed in Great Britain.
Canadian Journal of Chemistry, Band 61, Jul. 1983, Seiten 1383-1386.
Tetrahedron, Band 33, Nov. 1977, Seiten 1309-1319, Oxford, GB; M. Barrelle et al.
European Journal of Medicinal Chemistry-Chimie Therapeutique, Band 19, Jun. 1984, Seiten 495,500.

*Primary Examiner*—Alan L. Rotman
*Assistant Examiner*—Ba K. Trinh
*Attorney, Agent, or Firm*—Sprung Horn Kramer & Woods

[57] ABSTRACT

Combatting fungi and bacteria with aminomethyl-heterocyclic compounds of the formula pt,10
in which
$R^1$ represents hydrogen, alkyl, alkenyl, in each case optionally substituted tetrahydronaphthyl, decahydronaphthyl, cycloalkyl or cycloalkenyl, furthermore alkyl which is substituted by cycloalkyl, cycloalkenyl, cycloalkyloxy or cycloalkylthio, where the cyclic radicals may optionally be substituted, furthermore optionally substituted aryl, in addition alkyl which is substituted by aryl, aryloxy, arylthio, arylsulphinyl or arylsulphonyl, or alkenyl which is substituted by aryl, where the aryl radicals may in each case optionally be substituted;
$R^2$ represents hydrogen or methyl,
$R^3$ represents alkyl, alkenyl, alkinyl, alkoxyalkyl, hydroxyalkyl, hydroxyalkoxyalkyl, dialkoxyalkyl, or in each case optionally substituted cycloalkyl, cycloalkylalkyl, aryl, aralkyl, aralkenyl, furanylalkyl, tetrahydrofuranylalkyl, tetrahydropyranylalkyl, dioxolanylalkyl or dioxanylalkyl, and
X represents oxygen, sulphur or a $CH_2$ group,
or acid addition salts thereof.

Many of the compounds wherein $R^1$ has a narrower meaning are new.

9 Claims, No Drawings

PESTICIDES BASED ON SUBSTITUTED AMINOMETHYL HETEROCYCLIC COMPOUNDS

This is a division of application Ser. No. 423,607, filed Oct. 17, 1989, now U.S. Pat. No. 4,988,729, which is a continuation of application Ser. No. 184,865, filed Apr. 22, 1988, now abandoned.

The invention relates to the use of substituted aminomethylheterocyclic compounds, some of which are known, as pesticides.

It has already been disclosed that certain aminomethylheterocyclic compounds, such as, for example, tetrahydro-N,5-dimethyl-furfurylamine or 2,2-dimethyl-N-isopropyl-1,3-dioxolane-4-methanamine or N,2-dimethyl-1,3-oxathiolane-5-methanamine, or its hydrochloride, or cis-N-t-butyl-5-methyl-furfurylamine or N-cyclohexyl-2-methyl-2-phenyl-1,3-dioxolane-4-methanamine, inter alia, have certain pharmacological properties, such as, for example, antihypertensive, saluretic, parasympatholytic or muscarinergic properties or are used as intermediates in the preparation of pharmacologically active compounds (cf., for example, GB 1,031,916; DE-OS (German Published Specification) 2,810,732, DE-OS (German Published Specification) 2,757,922; Tetrahedron 33, 1309–1319 [1977]; Acta Pol. Pharm. 39, 33–39 [1982] or Europ. J. Med. Chem./-Chim. Ther. 19, 495–500 [1984], inter alia).

Nothing is hitherto known on the activity of these previously known compounds as pesticides.

It has furthermore been disclosed that certain aminoketals, such as, for example, 2-[3-(4-chlorophenoxy)-2-methyl-prop-2-yl]-2-methyl-4-[N,N-(di-n-butyl)-aminomethyl]-dioxolane or 2-[3-(4-methyl-phenoxy)-2-methyl-prop-2-yl]-2-methyl-4-[N,N-(di-n-butyl)-aminomethyl]-dioxolane or 2-[3-(4-chlorophenoxy)-2-methyl-prop-2-yl]-2-methyl-4-[N-methyl-N-(3-methyl-but-2-en-1-yl)-aminomethyl]-dioxolane, have good fungicidal properties (cf. EP 97,822).

However, the activity of these previously known compounds is not completely satisfactory in all areas of application, in particular at low application rates and concentrations.

It has been found that the substituted aminomethylheterocyclic compounds of the general formula (I)

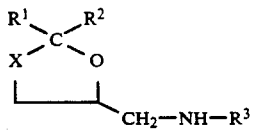

in which
$R^1$ represents hydrogen, alkyl, alkenyl, in each case optionally substituted tetrahydronaphthyl, decahydronaphthyl, cycloalkyl or cycloalkenyl, furthermore alkyl which is substituted by cycloalkyl, cycloalkenyl, cycloalkyloxy or cycloalkylthio, where the cyclic radicals may optionally be substituted, furthermore optionally substituted aryl, in addition alkyl which is substituted by aryl, aryloxy, arylthio, arylsulphinyl or arylsulphonyl, or alkenyl which is substituted by aryl, where the aryl radicals may in each case optionally be substituted;
$R^2$ represents hydrogen qr methyl,
$R^3$ represents alkyl, alkenyl, alkinyl, alkoxyalkyl, hydroxyalkyl, hydroxyalkoxyalkyl, dialkoxyalkyl, or in each case optionally substituted cycloalkyl, cycloalkylalkyl, aryl, aralkyl, aralkenyl, furanylalkyl, tetrahydrofuranylalkyl, tetrahydropyranylalkyl, dioxolanylalkyl or dioxanylalkyl, and
X represents oxygen, sulphur or a $CH_2$ group, some of which are known, and the acid addition salts thereof have a good action against pests, in particular against fungal pests.

The compounds of the formula (I) can exist as geometrical and/or optical isomers or isomer mixtures of various composition. The pure isomers and the isomer mixtures are claimed according to the invention.

Surprisingly, the substituted aminomethylheterocyclic compounds of the general formula (I) which can be used according to the invention exhibit a better activity against fungal pests than do the aminoketals which are known from the prior art, such as, for example, 2-[3-(4-chlorophenoxy)-2-methyl-prop-2-yl]-2-methyl-4-[N,N-(di-n-butyl)-aminomethyl]-dioxolane or 2-[3-(4-methyl-phenoxy)-2-methyl-prop-2-yl]-2-methyl-4-[N,N-(di-n-butyl)-aminomethyl]-dioxolane or 2-[3-(4-chlorophenoxy)-2-methyl-prop-2-yl]-2-methyl-4-[N-methyl-N-(3-methyl-but-2-en-1-yl)-aminomethyl]-dioxolane, which are similar compounds chemically and in view of their action.

Formula (I) provides a general definition of the substituted aminomethylheterocyclic compounds which can be used according to the invention. Compounds of the formula (I) which can preferably be used are those in which
$R^1$ represents hydrogen; in each case straight-chain or branched alkyl having 1 to 18 carbon atoms or alkenyl having 3 to 12 carbon atoms; in addition in each case represents optionally monosubstituted to polysubstituted tetrahydronaphthyl, decahydronaphthyl, cycloalkyl, cycloalkenyl, cycloalkylalkyl, cycloalkenylalkyl, cycloalkyloxyalkyl or cycloalkylthioalkyl in each case having, if appropriate, 5 to 7 carbon atoms in the cycloalkyl or cycloalkenyl parts and, if appropriate, 1 to 6 carbon atoms in the straight-chain or branched alkyl parts, the substituents being identical or different and suitable substituents being in each case: in each case straight-chain or branched alkyl, alkoxy, halogenoalkyl or halogenoalkoxy in each case having 1 to 6 carbon atoms and, if appropriate, 1 to 9 identical or different halogen atoms; and finally represents optionally monosubstituted to polysubstituted aryl, aralkyl, aryloxyalkyl, arylthioalkyl, arylsulphinylalkyl, arylsulphonylalkyl or arylalkenyl in each case having 6 to 10 carbon atoms in the aryl part and, if appropriate, up to 6 carbon atoms in the straight-chain or branched alkyl or alkenyl parts, the substituents being identical or different and suitable aryl substituents being in each case halogen, cyano, nitro, in each case straight-chain or branched alkyl, alkoxy, alkylthio, halogenoalkyl, halogenoalkoxy or halogenoalkylthio in each case having 1 to 6 carbon atoms and, if appropriate,1 to 9 identical or different halogen atoms, cyclohexyl or phenyl;
$R^2$ represents hydrogen or methyl,
$R^3$ represents in each case straight-chain or branched alkyl having 1 to 12 carbon atoms, alkenyl having 3 to 8 carbon atoms, alkinyl having 3 to 8 carbon atoms, hydroxyalkyl having 2 to 6 carbon atoms, alkoxyalkyl or dialkoxyalkyl in each case having 1 to 6 carbon atoms, or hydroxyalkoxyalkyl having 2 to 6 carbon atoms in the individual alkyl parts; or cycloalkyl or cycloalkylalkyl each of which has 3 to 7 carbon atoms in the cycloalkyl part and, if appropriate, 1 to 4 carbon atoms in the alkyl part and each of which is optionally monosubstituted to polysubstituted in the cycloalkyl part by identical or different substituents, suitable substituents being in each case: halogen and in each case straight-chain or branched alkyl, alkoxy, halogenoalkyl or halogenoalkoxy in each case having 1 to 4 carbon atoms and, if appropriate, 1 to 9 identical or different halogen atoms; and in addition represents aryl, arylalkyl or arylalkenyl each of which has 6 to 10 carbon atoms in the aryl part and, if appropriate, up to 6 carbon atoms in the in each case straight-chain or branched alkyl or alkenyl part and each of which is optionally monosubstituted to polysubstituted in the aryl part by identical or different substituents, suitable aryl substituents being in each case halogen, cyano, nitro and in each case straight-chain or branched alkyl, alkoxy, alkylthio, halogenoalkyl, halogenoalkoxy, halogenoalkylthio, alkoxycarbonyl or alkoximinoalkyl in each case having 1 to 4 carbon atoms in the individual alkyl parts and, if appropriate, 1 to 9 identical or different halogen atoms, or represents in each case straight-chain or branched furanylalkyl, tetrahydrofuranylalkyl, tetrahydropyranylalkyl, dioxolanylalkyl or dioxanylalkyl in each case having 1 to 4 carbon atoms in the alkyl part, suitable substituents being in each case: halogen and in each case straight-chain or branched alkyl, alkoxy, halogenoalkyl or halogenoalkoxy in each case having 1 to 4 carbon atoms and, if appropriate, 1 to 9 identical or different halogen atoms, and X represents oxygen, sulphur or a $CH_2$ group Compounds of the formula (I) which can particularly preferably be used according to the invention are those in which $R^1$ represents hydrogen; in each case straight-chain or branched alkyl having 1 to 12 carbon atoms or alkenyl having 3 to 8 carbon atoms, or tetrahydronaphthyl, decahydronaphthyl, cyclohexyl or cyclohexenyl each of which is optionally monosubstituted, disubstituted or trisubstituted by identical or different, straight-chain or branched alkyl having 1 to 4 carbon atoms; in addition represents an

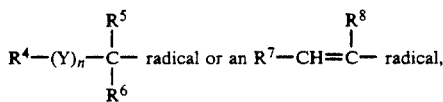

where
$R^4$ represents optionally monosubstituted, disubstituted or trisubstituted cyclohexyl, cyclohexenyl or phenyl, the substituents being identical or different and suitable cyclohexyl or cyclohexenyl substituents being in each case straight-chain or branched alkyl, alkoxy or halogenoalkyl in each case having 1 to 4 carbon atoms and, if appropriate, 1 to 9 identical or different halogen atoms, and where suitable phenyl substituents are: halogen, cyano, nitro, in each case straight-chain or branched alkyl, alkoxy, alkylthio, halogenoalkyl, halogenoalkoxy or halogenoalkylthio in each case having 1 to 4 carbon atoms and, if appropriate, 1 to 9 identical or different halogen atoms, cyclohexyl or phenyl, Y represents oxygen, sulphur, a —$CH_2$— group, an —O—$CH_2$— group, an —S—$CH_2$— group, a sulphinyl group, a sulphonyl group, an

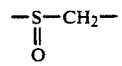

group or an —$SO_2$—$CH_2$— group, n represents a number 0 or 1,
$R^5$ represents hydrogen, methyl or ethyl,
$R^6$ represents hydrogen or methyl,
$R^7$ represents optionally monosubstituted, disubstituted or trisubstituted phenyl, the substituents being identical or different and suitable phenyl substituents being those mentioned in the case of $R^4$, and
$R^8$ represents methyl or ethyl,
$R^1$ in addition, represents in each case optionally monosubstituted, disubstituted or trisubstituted phenyl or naphthyl, the substituents being identical or different and suitable substituents being in each case: halogen, cyano, nitro, in each case straight-chain or branched alkyl, alkoxy, alkylthio, halogenoalkyl, halogenoalkoxy or halogenoalkylthio in each case having 1 to 4 carbon atoms and, if appropriate, 1 to 9 identical or different halogen atoms, cyclohexyl or phenyl;
$R^2$ represents hydrogen or methyl,
$R^3$ represents methyl, ethyl, n- or i-propyl, n-, i-, s- or t-butyl, n- or i-pentyl, n- or i-hexyl, n- or i-heptyl, n- or i-octyl, allyl, n- or i-butenyl, n- or i-pentenyl, propargyl, n- or i-butinyl, hydroxyethyl, hydroxypropyl, methoxyethyl, ethoxyethyl, propoxyethyl, butoxyethyl, methoxypropyl, ethoxypropyl, propoxypropyl, butoxypropyl, hydroxyethoxyethyl, dimethoxyethyl, dimethoxypropyl, diethoxyethyl, represents cyclopropyl, cyclopropylmethyl, cyclopropylethyl, cyclopropylpropyl, cyclopentyl, cyclopentylmethyl, cyclohexyl or cyclohexylmethyl, each of which is optionally monosubstituted to pentasubstituted by fluorine, chlorine, bromine, methyl, ethyl, n- or i-propyl, n-, i-, s- or t-butyl, these substituents being identical or different, or represents in each case optionally monosubstituted, disubstituted or trisubstituted phenyl, benzyl or phenylethyl, the substituents being identical or different and suitable substituents being in each case fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl, ethoxycarbonyl or methoximinomethyl; or represents furanylmethyl, tetrahydrofuranylmethyl, tetrahydropyranylmethyl, dioxolanylmethyl, dioxolanylethyl, dioxanylmethyl or dioxanylethyl, and X represents oxygen, sulphur or a $CH_2$ group.

Compounds of the formula (I) which can very particularly preferably be used according to the invention are those in which $R^1$ represents tetrahydronaphthyl, decahydronaphthyl, cyclohexyl or cyclohexenyl, each of which is optionally monosubstituted, disubstituted or trisubstituted by methyl or t-butyl, the substituents being identical or different, or represents an

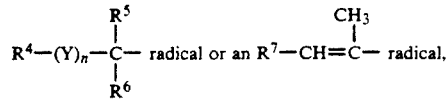

wherein

R⁴ represents cyclohexyl or cyclohexenyl, each of which is optionally monosubstituted, disubstituted or trisubstituted by methyl, i-propyl, t-butyl, methoxy, propoxy, butoxy, or trifluoromethyl, the substituents being identical or different, or represents phenyl which is optionally monosubstituted, disubstituted or trisubstituted by fluorine, chlorine, bromine, methyl, i-propyl, t-butyl, trifluoromethyl, trifluoromethoxy, trifluoromethylthio, methoxy, phenyl or cyclohexyl, the substituents being identical or different, Y represents oxygen, sulphur, a —CH₂— group, an —O—CH₂— group or an —S—CH₂— group, n represents a number 0 or 1, R⁵ represents methyl or ethyl, R⁶ represents hydrogen or methyl, and R⁷ represents phenyl which is optionally monosubstituted, disubstituted or trisubstituted by fluorine, chlorine, methyl, isopropyl, t-butyl, trifluoromethyl, trifluoromethoxy, trifluoromethylthio, methoxy, phenyl or cyclohexyl, the substituents being identical or different, R¹, in addition, represents phenyl or naphthyl, each of which is optionally monosubstituted, disubstituted or trisubstituted by fluorine, chlorine, bromine, methyl, i-propyl, t-butyl, trifluoromethyl, trifluoromethoxy, trifluoromethylthio, methoxy, phenyl or cyclohexyl, the substituents being identical or different, R² represents hydrogen or methyl, R³ represents methyl, ethyl, n- or i-propyl, n-, i-, s- or t-butyl, n- or i-pentyl, n- or i-hexyl, allyl, n- or i-butenyl, n- or i-pentenyl, propargyl, n- or i-butinyl, hydroxyethyl, hydroxypropyl, methoxyethyl, methoxypropyl, ethoxyethyl, ethoxypropyl, hydroxyethoxyethyl, dimethoxyethyl, diethoxyethyl, dichlorocyclopropylmethyl, dimethylcyclopropylmethyl, dichlorodimethylcyclopropylmethyl, cyclopentyl, or cyclohexyl or cyclohexylmethyl, each of which is optionally monosubstituted, disubstituted or trisubstituted by methyl, or furanylmethyl, tetrahydrofuranylmethyl, tetrahydropyranylmethyl, dioxolanylmethyl, dioxolanylethyl or dioxanylmethyl, and X represents oxygen, sulphur or a CH₂ group.

Plant-tolerated addition products of acids and those substituted aminomethylheterocyclic compounds of the formula (I) in which the substituents X, R¹, R² and R³ have the meanings which have already been mentioned as being preferred for these substituents are also preferred compounds which can be used according to the invention.

The acids which can be added preferably include hydrohalic acids, such as, for example, hydrochloric acid and hydrobromic acid, in particular hydrochloric acid, furthermore phosphoric acid, nitric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid; sulphonic acids, such as p-toluenesulphonic acid and 1,5-naphthalenedisulphonic acid, and saccharin.

Reference may be made individually to the compounds mentioned in the preparation examples.

Some of the substituted aminomethylheterocyclic compounds which can be used according to the invention are known (cf., for example, GB 1,031,916; DE-OS (German Published Specification) 2,810,732; DE-OS (German Published Specification) 2,757,922; Tetrahedron 33, 1309-1319 [1977]; Acta Pol. Pharm 39, 33-39 [1982] or Europ. J. Med. Chem./Chim Ther. 19, 495-500 [1984]), or can be prepared by analogous processes, thus, for example, by the processes given below for the compounds of the formula (Ia).

Substituted aminomethylheterocyclic compounds of the formula (Ia)

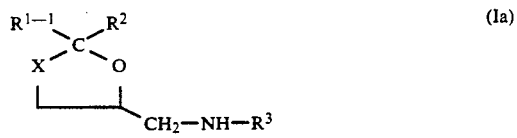

in which

R¹⁻¹ represents substituted phenyl, in each case optionally substituted cycloalkyl, cycloalkenyl, tetrahydronaphthyl, decahydronaphthyl or naphthyl, an

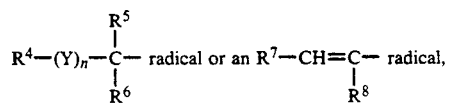

where

R⁴ represents in each case optionally substituted cyclohexyl, cyclohexenyl or phenyl, Y represents oxygen, sulphur, a —CH₂— group an —O—CH₂— group, an —S—CH₂— group, a sulphinyl group, a sulphonyl group, an

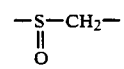

group or an —SO₂—CH₂— group, n represents a number 0 or 1,

R⁵ represents hydrogen, methyl or ethyl,

R⁶ represents hydrogen, methyl or ethyl,

R⁷ represents optionally monosubstituted, disubstituted or trisubstituted phenyl, the substituents being identical or different, and R⁸ represents methyl or ethyl;

R² represents hydrogen or methyl,

R³ represents alkyl, alkenyl, alkinyl, alkoxyalkyl, hydroxyalkyl, hydroxyalkoxyalkyl, dialkoxyalkyl, in each case optionally substituted cycloalkyl, cycloalkylalkyl, aryl, aralkyl, aralkenyl, furanylalkyl, tetrahydrofuranylalkyl, tetrahydropyranylalkyl, dioxolanylalkyl or dioxanylalkyl, and X represents oxygen, sulphur or a —CH₂— group, the acid addition salts thereof and the geometrical and-/or optical isomers or isomer mixtures thereof, were hitherto not known.

The hitherto unknown substituted aminomethylheterocyclic compounds of the formula (Ia)

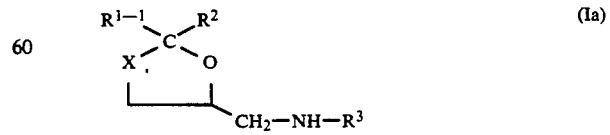

in which

R¹⁻¹ represents substituted phenyl, in each case optionally substituted napthyl, cycloalkyl, cycloalkenyl, tetrahydronaphthyl or decahydronaphthyl, an

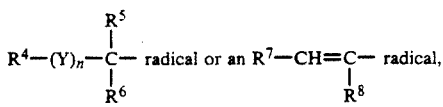 radical or an $R^7$—CH=C— radical, where
$R^4$ represents in each case optionally substituted cyclohexyl, cyclohexenyl or phenyl,
Y represents oxygen, sulphur, a —CH$_2$— group an —O—CH$_2$— group, an —S—CH$_2$- group, a sulphinyl group, a sulphonyl group, an

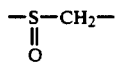

group or an —SO$_2$—CH$_2$— group,
n represents a number 0 or 1,
$R^5$ represents hydrogen, methyl or ethyl,
$R^6$ represents hydrogen, methyl or ethyl,
$R^7$ represents optionally monosubstituted, disubstituted or trisubstituted phenyl, the substituents being identical or different, and
$R^2$ represents hydrogen or methyl,
$R^3$ represents alkyl, alkenyl, alkinyl, alkoxyalkyl, hydroxyalkyl, hydroxyalkoxyalkyl, dialkoxyalkyl, in each case optionally substituted cycloalkyl, cycloalkylalkyl, aryl, aralkyl, aralkenyl, furanylalkyl, tetrahydrofuranylalkyl, tetrahydropyranylalkyl, dioxolanylalkyl or dioxanylalkyl, and
X represents oxygen, sulphur or a —CH$_2$— group,
the acid addition salts thereof and the geometrical and/or optical isomers or isomer mixtures thereof, are obtained analogously to known processes, when (a) heterocyclic compounds of the formula (II)

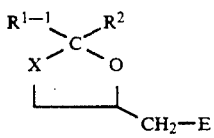 (II)

in which
$R^{1-1}$ and $R^2$ have the abovementioned meaning, and
E represents an electron-withdrawing leaving group, are reacted with amines of the formula (III)

$H_2N—R^3$ (III)

in which
$R^3$ has the abovementioned meaning, if appropriate in the presence of a diluent and if appropriate in the presence of an acid-binding agent, or when
(b) the substituted aminomethylheterocyclic compounds of the formula (Ia-1)

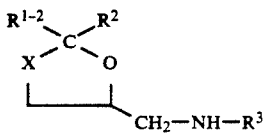 (Ia-1)

in which
$R^{1-2}$ represents substituted phenyl, optionally substituted naphthyl, an

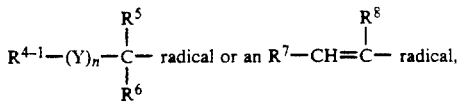 radical or an $R^7$—CH=C— radical,

X, $R^2$, $R^3$, $R^5$, $R^6$, $R^7$ and $R^8$ the above-mentioned meaning, and
$R^{4-1}$ represents optionally substituted phenyl, obtainable with the aid of process (a) are hydrogenated using hydrogen in the presence of a catalyst and if appropriate in the presence of a diluent.

Formula (Ia) provides a general definition of the new substituted aminomethylheterocyclic compounds. Preferred compounds of the formula (Ia) are those in which $R^{1-1}$ represents monosubstituted to polysubstituted phenyl, the substituents being identical or different, or optionally monosubstituted to polysubstituted naphthyl, the substituents being identical or different and suitable substituents being in each case: halogen, cyano, nitro, in each case straight-chain or branched alkyl, alkoxy, alkylthio, halogenoalkyl, halogenoalkoxy, halogenoalkylthio in each case having 1 to 6 carbon atoms and, if appropriate, 1 to 9 identical or different halogen atoms, cyclohexyl or phenyl; in addition represents in each case optionally monosubstituted to polysubstituted cycloalkyl or cycloalkenyl in each case having 5 to 7 carbon atoms, tetrahydronaphthyl or decahydronaphthyl, the substituents being identical or different and suitable substituents being in each case: in each case straight-chain or branched alkyl, halogenoalkyl or halogenoalkoxy in each case having 1 to 6 carbon atoms and, if appropriate, 1 to 9 identical or different halogen atoms; in addition represents an

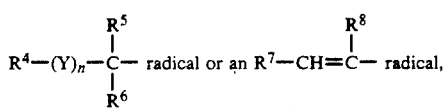 radical or an $R^7$—CH=C— radical, where
$R^4$ represents in each case optionally monosubstituted, disubstituted or trisubstituted cyclohexyl, cyclohexenyl or phenyl, the substituents being identical or different and suitable cyclohexyl or cyclohexenyl substituents being in each case straight-chain or branched alkyl, alkoxy, or halogenoalkyl in each case having 1 to 4 carbon atoms and, if appropriate, 1 to 9 halogen atoms, and suitable phenyl substituents being: halogen, cyano, nitro, in each case straight-chain or branched alkyl, alkoxy, alkylthio, halogenoalkyl, halogenoalkoxy or halogenoalkylthio in each case having 1 to 4 carbon atoms and, if appropriate, 1 to 9 identical or different halogen atoms, cyclohexyl or phenyl,
Y represents oxygen, sulphur, a —CH$_2$— group, an —O—CH$_2$— group, an —S—CH$_2$— group, a sulphinyl group, a sulphonyl group, an

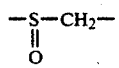

group or an —SO$_2$—CH$_2$— group,
n represents a number 0 or 1,
$R^5$ represents hydrogen, methyl or ethyl, $R^6$ represents hydrogen or methyl, $R^7$ represents optionally monosubstituted, disubstituted or trisubstituted phenyl, the substituents being identical or different and suitable phenyl substituents being those mentioned in the case of $R^4$, and $R^8$ represents methyl or ethyl, $R^2$ represents hydrogen or methyl, $R^3$ represents in each case straight-chain or branched alkyl having 1 to 12 carbon atoms, alkenyl having 3 to 8 carbon atoms, alkinyl having 3 to 8 carbon atoms, hydroxyalkyl having 2 to 6 carbon atoms, alkoxyalkyl or dialkoxyalkyl in each case having 1 to 6 carbon atoms or hydroxyalkoxyalkyl having 2 to 6 carbon atoms in the individual alkyl parts, or cycloalkyl or cycloalkylalkyl in each case having 3 to 7 carbon atoms in the cycloalkyl part and, if appropriate, 1 to 4 carbon atoms in the alkyl part and each of which is optionally monosubstituted to polysubstituted in the cycloalkyl part, the substituents being identical or different and suitable substituents being in each case halogen and in each case straight-chain or branched alkyl, alkoxy, halogenoalkyl or halogenoalkoxy in each case having 1 to 4 carbon atoms and, if appropriate, 1 to 9 identical or different halogen atoms; in addition represents aryl, arylalkyl or arylalkenyl in each case having 6 to 10 carbon atoms in the aryl part and, f appropriate, up to 6 carbon atoms in each straight-chain or branched alkyl or alkenyl part and each of which is optionally monosubstituted or polysubstituted in the aryl part by identical or different substituents, suitable aryl substituents being in each case halogen, cyano, nitro and in each case straight-chain or branched alkyl, alkoxy, alkylthio, halogenoalkyl, halogenoalkoxy, halogenoalkylthio, alkoxycarbonyl or alkoximinoalkyl in each case having 1 to 4 carbon atoms in the individual alkyl parts and, if appropriate, 1 to 9 identical or different halogen atoms, or represents in each case straight-chain or branched furanylalkyl, tetrahydrofuranylalkyl, tetrahydropyranylalkyl, dioxolanylalkyl or dioxanylalkyl in each case having 1 to 4 carbon atoms in the alkyl part, and X represents oxygen, sulphur or a $CH_2$ group.

Particularly preferred compounds according to the invention are those in which, in the formula (Ia), $R^{1\text{-}1}$ represents monosubstituted, disubstituted or trisubstituted phenyl, the substituents being identical or different, or optionally monosubstituted, disubstituted or trisubstituted naphthyl, the substituents being identical or different and suitable substituents being in each case: fluorine, chlorine, bromine, methyl, i-propyl, t-butyl, trifluoromethyl, trifluoromethoxy, trifluoromethylthio, methoxy, phenyl or cyclohexyl; in addition represents in each case optionally monosubstituted, disubstituted or trisubstituted cyclohexyl, cyclohexenyl, tetrahydronaphthyl or decahydronaphthyl, the substituents being identical or different and suitable substituents being in each case: straight-chain or branched alkyl having 1 to 4 carbon atoms; in addition represents an

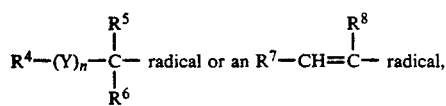

where $R^4$ represents cyclohexyl or cyclohexenyl, each of which is optionally monosubstituted, disubstituted or trisubstituted by methyl, i-propyl, t-butyl, methoxy, propoxy, butoxy or trifluoromethyl, the substituents being identical or different, or represents phenyl which is optionally monosubstituted, disubstituted or trisubstituted by fluorine, chlorine, bromine, methyl, i-propyl, t-butyl, trifluoromethyl, trifluoromethoxy, trifluoromethylthio, methoxy, phenyl or cyclohexyl, the substituents being identical or different, Y represents oxygen, sulphur, a $—CH_2—$ group, an $—O—CH_2—$ group or an $—S—CH_2—$ group, n represents a number 0 or 1, $R^5$ represents methyl or ethyl, $R^6$ represents hydrogen or methyl, and $R^7$ represents phenyl which is optionally monosubstituted, disubstituted or trisubstituted by fluorine, chlorine, methyl, isopropyl, t-butyl, trifluoromethyl, trifluoromethoxy, trifluoromethylthio, methoxy, phenyl or cyclohexyl, the substituents being identical or different, and $R^8$ represents methyl or ethyl, $R^2$ represents hydrogen or methyl, $R^3$ represents methyl, ethyl, n- or i-propyl, n-, i-, s- or t-butyl, n- or i-pentyl, n- or i-hexyl, n- or i-heptyl, n- or i-octyl, allyl, n- or i-butenyl, n- or i-pentenyl, propargyl, n- or i-butinyl, hydroxyethyl, hydroxypropyl, methoxyethyl, ethoxyethyl, propoxyethyl, butoxyethyl, methoxypropyl, ethoxypropyl, propoxypropyl, butoxypropyl, hydroxyethoxyethyl, dimethoxyethyl, dimethoxypropyl, diethoxyethyl, represents cyclopropyl, cyclopropylmethyl, cyclopropylethyl, cyclopropylpropyl, cyclopentyl, cyclopentylmethyl, cyclohexyl or cyclohexylmethyl, each of which is optionally monosubstituted to pentasubstituted by fluorine, chlorine, bromine, methyl, ethyl, n- or i-propyl, n-, i-, s- and/or t-butyl, the substituents being identical or different, or represents in each case optionally monosubstituted, disubstituted or trisubstituted phenyl, benzyl or phenylethyl, the substituents being identical or different and suitable substituents being in each case: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl, ethoxycarbonyl or methoxyiminomethyl; or represents furanylmethyl, tetrahydrofuranylmethyl, tetrahydropyranylmethyl, dioxolanylmethyl, dioxolanylethyl, dioxanylmethyl or dioxanylethyl, and X represents oxygen, sulphur or a $CH_2$ group.

Plant-compatible addition products of acids and those substituted aminomethylheterocyclic compounds of the formula (Ia) in which the substituents X, $R^{1\text{-}1}$, $R^2$ and $R^3$ have the meanings which have already been mentioned as being preferred for these substituents are also preferred compounds according to the invention.

The acids which can be added preferably include hydrohalic acids, such as, for example, hydrochloric acid and hydrobromic acid, in particular hydrochloric acid, furthermore phosphoric acid, nitric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, sulphonic acids, such as p-toluenesulphonic acid and 1,5-naphthalenedisulphonic acid, and also saccharin.

If, for example, 4-chloromethyl-2-(4-chlorophenyl)-2-methyl-1,3-dioxolane and methylamine are used as starting materials, the course of the reaction of preparation process (a) may be represented by the following equation:

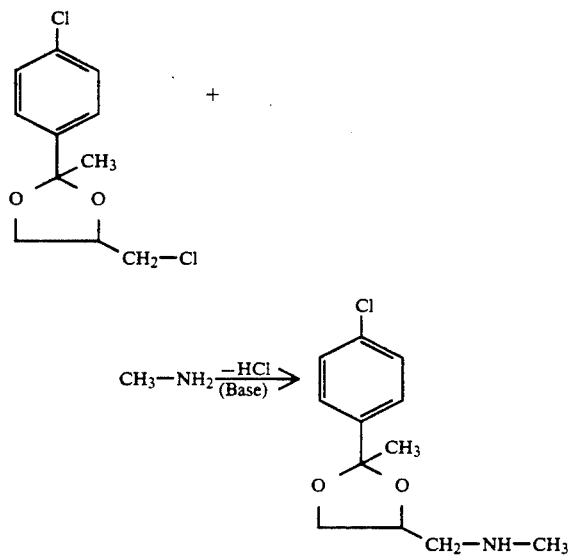

If, for example, 2-(4-t-butylphenyl)-2-methyl-5-(N-ethylaminomethyl)-tetrahydrofuran is used as starting compound, the course of the reaction of preparation process (b) may be represented by the following equation:

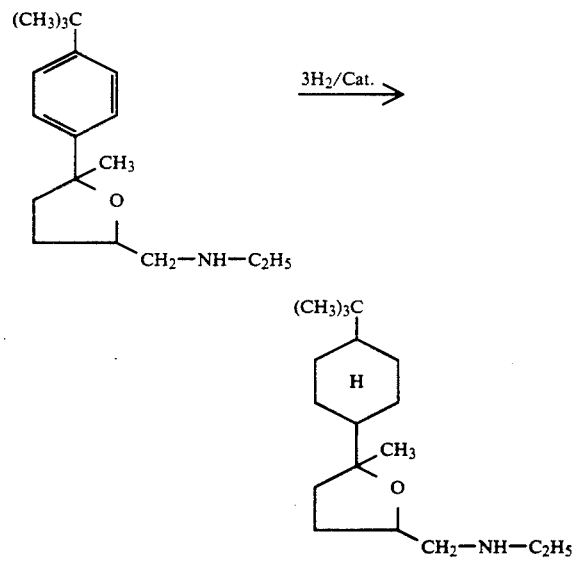

Formula (II) provides a general definition of the heterocyclic compounds which are required as starting materials for carrying out preparation process (a). In this formula (II), $R^{1-1}$ and $R^2$ preferably represent those radicals which have already been mentioned in connection with the description of the substances of the formula (Ia) according to the invention as being preferred for these substituents.

E preferably represents halogen, in particular chlorine, bromine or iodine, or in each case optionally substituted alkylsulphonyloxy or arylsulphonyloxy, such as, for example, methanesulphonyloxy or p-toluenesulphonyloxy.

The heterocyclic starting compounds of the formula (II) are known or can be obtained analogously to known processes (cf., for example, EP 97,822, DE-OS (German Published Specification) 3,413,996; DE-OS (German Published Specification) 3,324,769 or DE-OS (German Published Specification) 3,328,151).

Formula (III) provides a general definition of the amines which are furthermore required as starting materials for carrying out preparation process (a). In this formula (III), $R^3$ preferably represents those radicals which have already been mentioned in connection with the description of the substances of the formula (Ia) according to the invention as being preferred for this substituent.

The amines of the formula (III) are compounds which are generally known from organic chemistry.

Formula (Ia-1) provides a general definition of the substituted aminomethylheterocyclic compounds which are required as starting materials for carrying out preparation process (b). In this formula (Ia-1), $R^2$ and $R^3$ preferably represent those radicals which have already been mentioned in connection with the description of the substances of the formula (Ia) according to the invention as being preferred for these substituents.

$R^{1-2}$ preferably represents monosubstituted to polysubstituted phenyl, the substituents being identical or different, or optionally monosubstituted or polysubstituted naphthyl, the substituents being identical or different and suitable substituents being in each case: halogen, cyano, nitro, in each case straight-chain or branched alkyl, alkoxy, alkylthio, halogenoalkyl, halogenoalkoxy, halogenoalkylthio in each case having 1 to 6 carbon atoms and, if appropriate, 1 to 9 identical or different halogen atoms, cyclohexyl or phenyl; in addition represents an

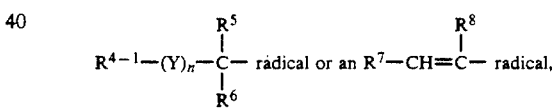

where $R^{4-1}$ represents optionally monosubstituted, disubstituted or trisubstituted phenyl, the substituents being identical or different and suitable substituents being: halogen, cyano, nitro, in each case straight-chain or branched alkyl, alkoxy, alkylthio, halogenoalkyl, halogenoalkoxy or halogenoalkylthio in each case having 1 to 4 carbon atoms and, if appropriate, 1 to 9 identical or different halogen atoms, cyclohexyl or phenyl, Y represents oxygen, sulphur, a —CH$_2$— group, an —O—CH$_2$— group or an —S—CH$_2$— group a sulphinyl group, a sulphonyl group, an

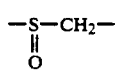

group or an —SO$_2$—CH$_2$— group, n represents a number 0 or 1, $R^5$ represents hydrogen, methyl or ethyl, $R^6$ represents hydrogen or methyl, $R^7$ represents optionally monosubstituted, disubstituted or trisubstituted phenyl, the substituents being identical or different and suitable phenyl substituents being those mentioned in the case of $R^{4-1}$, and $R^8$ represents methyl or ethyl.

$R^{1-2}$ particularly preferably represents in each case monosubstituted, disubstituted or trisubstituted phenyl or naphthyl, the substituents being identical or different and suitable substituents being fluorine, chlorine, bromine, methyl, i-propyl, t-butyl, trifluoromethyl, trifluoromethoxy, trifluoromethylthio, methoxy, phenyl or cyclohexyl; in addition represents an

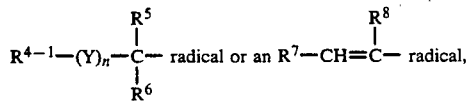

where $R^{4-1}$ represents phenyl which is optionally monosubstituted, disubstituted or trisubstituted by fluorine, chlorine, bromine, methyl, i-propyl, t-butyl, trifluoromethyl, trifluoromethoxy, trifluoromethylthio, methoxy, propoxy, butoxy, phenyl or cyclohexyl, the substituents being identical or different, Y represents oxygen, sulphur, a —$CH_2$— group, an —O—$CH_2$— group or an —S—$CH_2$— group, n represents a number 0 or 1, $R^5$ represents methyl or ethyl, $R^6$ represents hydrogen or methyl, $R^7$ represents phenyl which is optionally monosubstituted, disubstituted or trisubstituted by fluorine, chlorine, methyl, isopropyl, t-butyl, trifluoromethyl, trifluoromethoxy, trifluoromethylthio, methoxy, phenyl or cyclohexyl, the substituents being identical or different, and $R^8$ represents methyl or ethyl.

The substituted aminomethylheterocyclic compounds of the formula (Ia-1) are compounds according to the invention and can be obtained with the aid of preparation process (a).

Suitable diluents for carrying out preparation process (a) are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, sulphoxides, such as dimethyl sulphoxide, or alcohols, such as propanol or butanol. However, preparation process (a) can also be carried out without addition of a diluent.

Preparation process (a) can also be carried out, if appropriate, in a two-phase system, such as, for example, water/toluene or water/dichloromethane, if appropriate in the presence of a phase-transfer catalyst Examples of such catalysts which may be mentioned are: tetrabutylammonium iodide, tetrabutylammonium bromide, tributyl-methylphosphonium bromide, trimethyl-$C_{13}/C_{15}$-alkylammonium chloride, dibenzyl-dimethylammonium methylsulphate, dimethyl-$C_{12}/C_{14}$-alkyl-benzylammonium chloride, tetrabutylammonium hydroxide, 15-crown-5, 18-crown-6, triethylbenzylammonium chloride and trimethylbenzylammonium chloride.

Suitable acid-binding agents for carrying out preparation process (a) are all inorganic and organic bases which can conventionally be used. Alkali metal hydrides, hydroxides, amides, carbonates or hydrogen carbonates, such as, for example, sodium hydride, sodium amide, sodium hydroxide, sodium carbonate or sodium hydrogen carbonate, or alternatively tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU), are preferably used.

However, it is also possible to simultaneously use the amine of the formula (III) used as reactant as a reaction auxiliary and/or as a diluent, in an appropriate excess.

The reaction temperatures may be varied within a relatively wide range when carrying out preparation process (a). In general, the process is carried out at temperatures between 50° C. and 250° C., preferably at temperatures between 80° C. and 200° C.

Preparation process (a) is usually carried out at atmospheric pressure However, it is also possible to carry out the process at an increased pressure between 1.5 and 5.0 atu.

To carry out preparation process (a), 1.0 to 5.0 moles, preferably 1.0 to 3.0 moles, of amine of the formula (III) and, if appropriate, 1.0 to 5.0 moles, preferably 1.0 to 3.0 moles, of acid-binding agent are generally employed per mole of heterocyclic compound of the formula (II). The reaction is carried out and the reaction products of the formula (Ia) are worked up and isolated by conventional methods.

Suitable diluents for carrying out preparation process (b) are likewise inert organic solvents. These include, in particular, aliphatic or alicyclic, optionally halogenated hydrocarbons, such as, for example, benzine, petroleum ether, hexane or cyclohexane; ethers, such as diethyl ether, dioxane, tetrahydrofuran or ethylene glycol dimethyl or diethyl ether; esters, such as ethyl acetate, or alcohols, such as methanol, ethanol or isopropanol.

Catalysts which can be employed for carrying out preparation process (b) are all conventional hydrogenation catalysts. Noble metal catalysts, noble metal oxide catalysts or noble metal hydroxide catalysts, or so-called Raney catalysts, such as, in particular, platinum, platinum oxide, palladium, nickel and ruthenium, if appropriate on a suitable support, such as charcoal, aluminum oxide or silicon dioxide, are preferably used.

The reaction temperatures may be varied within a relatively wide range when carrying out the preparation process. In general, the process is carried out at temperatures between 20° C. and 250° C., preferably at temperatures between 20° C. and 200° C.

Preparation process (b) is carried out, if appropriate, under increased pressure. In general, the process is carried out in a pressure range between 1 and 250 atm, preferably between 1 and 150 atm.

To carry out preparation process (b), 0.001 to 0.1 mole, preferably 0.01 to 0.05 mole, of hydrogenation catalyst are added per mole of substituted aminomethylheterocyclic compound of the formula (Ia-1), and hydrogen is added in an autoclave until the necessary pressure has been reached. The reaction is carried out and the reaction products are worked up and isolated by conventional methods.

The following acids are preferably suitable for the preparation of plant-tolerated acid addition salts of the compounds of the formula (Ia): hydrohalic acids, such as, for example, hydrochloric acid and hydrobromic acid, in particular hydrochloric acid, furthermore phosphoric acid, nitric acid, sulphuric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, sulphonic acids, such as, for example, p-toluenesulphonic acid and 1,5-naphthalenedisulphonic acid, and also saccharin.

The acid addition salts of the compounds of the formula (Ia) can be obtained in a simple fashion by conventional salt-formation methods, such as, for example, by dissolving a compound of the formula (Ia) in a suitable inert solvent and adding the acid, such as for example, hydrochloric acid, and isolated in a known fashion, for example by filtering off, and purified, if appropriate, by washing with an inert organic solvent.

The compounds which can be used according to the invention have a strong action against pests and can be employed in practice for combating undesired harmful organisms. The active compounds are suitable for use as plant-protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation Xanthomonas species, such as, for example, Xanthomonas campestris pv. oryzae; Pseudomonas species, such as, for example, *Pseudomonas syringae* pv. lachrymans; Erwinia species, such as, for example, *Erwinia amylovora*; Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubense*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *puccinia recondita*; Tilletia species, such as, for example, *Tilletia caries*; Ustilago species, such as, for example, *Ustilago nuda* or Ustilago avenae; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentration required for combating plant diseases, permits treatment of above-ground parts of plants, of vegetative propagation stock and seeds, and of the soil.

In this case, the active compounds which can be used according to the invention can be employed particularly successfully for combating cereal diseases, such as, for example, against the pathogen of true cereal mildew (*Erysiphe graminis*) or against the pathogen of brown-spot disease of wheat (*Cochliobolus sativus*), against the pathogen of net blotch of barley (*Pyrenophora teres*) or against the pathogen of glume blotch of wheat (*Septoria nodorum*), for combating rice diseases, such as, for example, against the pathogen of rice spot disease (Pyricularia oryzae), or for combating diseases in fruit-growing, such as, for example, against the pathogen of apple scab (Venturia inaequalis). At the same time, the active compounds which can be used according to the invention also have a systemic activity in addition to good protective properties. In addition, the active compounds which can be used according to the invention have a good bactericidal action and an excellent in vitro activity.

Depending on their particular physical and /or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as, fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholiids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuff, azo dyestuffs and metal phthalocyanine dyestuffs, and trace nutrients such as salts of iron, manganese, boron, copper, colbalt, molybdenum and zinc.

The formulations in general contain between 0.1 and 95 per cent by weight of active compound, preferably between 0.5 and 90%.

The active compounds which can be used according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomising, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

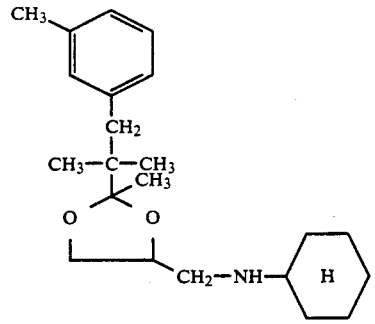

(Process a)

28.3 g (0.1 mol) of 4-chloromethyl-2-methyl-2-[1-(3-methylphenyl)-2-methyl-prop-2-yl]-1,3-dioxolane and 56.4 g (0.5 mol) of cyclohexylamine are heated for 16 hours at the reflux temperature (134° C.), cooled, taken up in 250 ml of ethyl acetate, washed four times with 150 ml of water in each case, dried over sodium sulphate, evaporain vacuo and purified by column chromatography (silica gel 60; ethyl acetate/ethyl acetate-ethanol 1:1).

27.5 g (80% of theory) of 4-cyclohexylamino-methyl-2-methyl-2-[1-(3-methylphenyl)-2-methyl-prop-2-yl]-1,3-dioxolane of refractive index $n_D^{20}$ 1.5133 are obtained.

Preparation of the starting compound

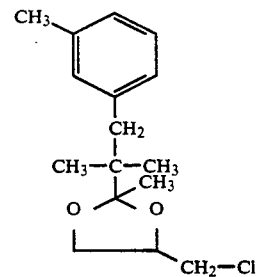

120 g (0.63 mol) of 3,3-dimethyl-4-(3-methylphenyl)-butan-2-one and 139.2 g (1.26 mol) of 3-chloropropane-1,2-diol are refluxed for 30 hours on a water separator together with 12 g (0.063 mol) of p-toluenesulphonic acid in 1.2 l of toluene. The cooled reaction mixture is washed twice with 500 ml of a saturated aqueous sodium hydrogen carbonate solution in each case, dried over sodium sulphate, and evaporated in vacuo, and the residue is distilled in a high vacuum.

123.3 g (70% of theory) of 4-chloromethyl-2-methyl-2-[1-(3-methylphenyl)-2-methyl-prop-2-yl]-1,3-dioxolane of boiling point 100° C. at 0.13 mbar are obtained.

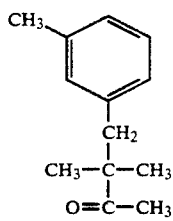

A solution of 421.8 g (3 mol) of 3-methylbenzyl chloride and 515 g (6 mol) of methyl isopropyl ketone is added dropwise while stirring to a mixture of 336 g (6 mol) of powdered potassium hydroxide and 48.2 g (0.015 mol) of tetrabutylammonium bromide in 2 l of cyclohexane at the reflux temperature. When the addition is complete, the mixture is heated for 44 hours at the reflux temperature on a water separator, the solid potassium hydroxide is separated from the cooled reaction mixture by filtering off under suction through Celite, the filtrate is evaporated in vacuo, and the residue is distilled in a high vacuum.

420 g (37% of theory) of 3,3-dimethyl-4-(3-methylphenyl)-butan-2-one of boiling point 74° C. at 0.35 mbar are obtained.

Example 2

(Process b)

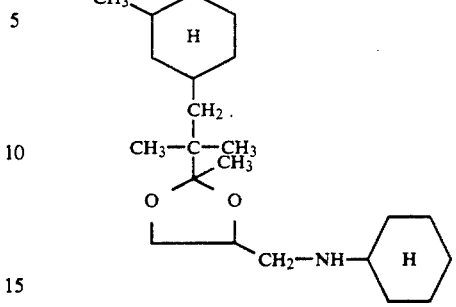

40 g (0.116 mol) of 4-cyclohexylaminomethyl-2-methyl-2-[1-(3-methylphenyl)-2-methyl-prop-2-yl]-1,3-dioxolane are hydrogenated in 300 ml of isopropanol for 2.5 hours at 130° C. and at a hydrogen pressure of 190 to 200 bar together with 8 g of ruthenium carbon catalyst (5%). For work-up, the catalyst is filtered off and the solvent is removed by distillation in vacuo.

36.8 g (91% of theory) of 4-cyclohexylamino-methyl-2-methyl-2-[1-(3-methylcylohexyl)-2-methyl-prop-2-yl]-1,3-dioxolane are obtained as an oil of refractive index $n_D^{20}$ 1.4839.

The following substituted aminomethylheterocyclic compounds of the general formula (I) are obtained in a corresponding fashion and in accordance with the general instructions for the preparation:

(I)

| Example No. | $R^1$ | $R^2$ | $R^3$ | X | physical properties |
|---|---|---|---|---|---|
| 3 | ![2-methylnaphthyl] | $CH_3$ | $CH_3$ | O | $^1$H-NMR*): 2.4–2.9; 7.4–8.05 |
| 4 | Cl—C₆H₄—CH₂— | $CH_3$ | $CH_3$ | O | $^1$H-NMR*): 2.2–3.0; 7.15–7.3 |
| 5 | Cl—C₆H₄—CH₂— | $CH_3$ | $C_2H_5$ | O | $^1$H-NMR*): 2.3–2.7; 7.15–7.3 |
| 6 | Cl—C₆H₄—CH₂— | $CH_3$ | $CH_2=CH-CH_2-$ | O | $^1$H-NMR*): 7.15–7.3 |
| 7 | Cl—C₆H₄—CH₂— | $CH_3$ | $CH_3-(CH_2)_2-$ | O | $^1$H-NMR*): 7.15–7.3 |

-continued
$$\begin{array}{c} R^1 \quad R^2 \\ X \diagdown\diagup O \\ | \\ CH_2-NH-R^3 \end{array} \quad (I)$$
| Example No. | R¹ | R² | R³ | X | physical properties |
|---|---|---|---|---|---|
| 8 | 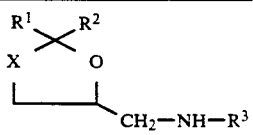 | CH₃ | CH₃—(CH₂)₃— | O | ¹H-NMR*⁾: 7.17–7.3 |
| 9 | 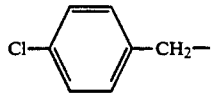 | CH₃ | CH₃—(CH₂)₄— | O | ¹H-NMR*⁾: 7.15–7.3 |
| 10 | 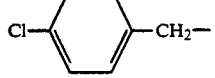 | CH₃ | CH₃—(CH₂)₅— | O | ¹H-NMR*⁾: 7.15–7.3 |
| 11 |  | CH₃ | (CH₃)₂CH— | O | ¹H-NMR*⁾: 7.15–7.3 |
| 12 | 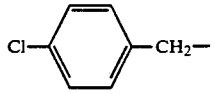 | CH₃ | CH₃—CH₂—CH(CH₃)— | O | ¹H-NMR*⁾: 7.15–7.3 |
| 13 | 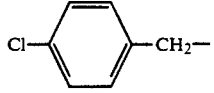 | CH₃ | CH₃ | O | ¹H-NMR*⁾: 7.3–7.85; 8.5–8.6 |
| 14 | 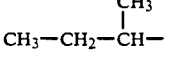 | CH₃ | C₂H₅ | O | ¹H-NMR*⁾: 7.35–7.9; 8.55–8.65 |
| 15 | 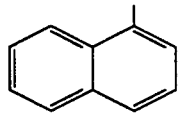 | CH₃ | CH₂=CH—CH₂— | O | ¹H-NMR*⁾: 7.35–7.9; 8.55–8.65 |
| 16 | 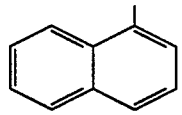 | CH₃ | CH₃—(CH₂)₂— | O | ¹H-NMR*⁾: 7.35–7.85; 8.55–8.65 |
| 17 | 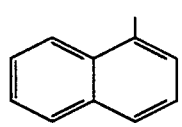 | CH₃ | CH₃—(CH₂)₃— | O | ¹H-NMR*⁾: 7.35–7.9; 8.55–8.65 |
| 18 | 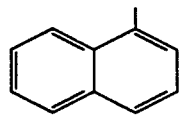 | CH₃ | CH₃—(CH₂)₄— | O | ¹H-NMR*⁾: 7.3–7.9; 8.55–8.65 |

-continued

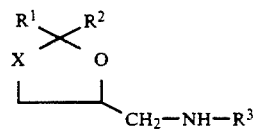
(I)

| Example No. | R¹ | R² | R³ | X | physical properties |
|---|---|---|---|---|---|
| 19 | 1-naphthyl | $CH_3$ | $CH_3-(CH_2)_5-$ | O | $^1$H-NMR*): 7.35–7.85; 8.55–8.65 |
| 20 | 1-naphthyl | $CH_3$ | $(CH_3)_2CH-$ | O | $^1$H-NMR*): 7.35–7.85; 8.55–8.65 |
| 21 | 1-naphthyl | $CH_3$ | $C_2H_5-CH(CH_3)-$ | O | $^1$H-NMR*): 7.35–7.85; 8.55–8.65 |
| 22 | 4-Cl-C₆H₄-CH₂- | $CH_3$ | $(C_2H_5)_2CH-$ | O | $^1$H-NMR*): 7.15–7.3 |
| 23 | 1-naphthyl | $CH_3$ | $(C_2H_5)_2CH-$ | O | $^1$H-NMR*): 7.35–7.85; 8.55–8.65 |
| 24 | 4-Cl-C₆H₄-CH₂-C(CH₃)₂- | H | $CH_3$ | O | $^1$H-NMR*): 7.05, 7.3 |
| 25 | 4-Cl-C₆H₄-CH₂-C(CH₃)₂- | H | $C_2H_5$ | O | $^1$H-NMR*): 7.05–7.3 |
| 26 | 4-Cl-C₆H₄-CH₂-C(CH₃)₂- | H | $CH_3-(CH_2)_3-$ | O | $^1$H-NMR*): 7.05–7.3 |
| 27 | 4-Cl-C₆H₄-CH₂-C(CH₃)₂- | H | $(CH_3)_2CH-$ | O | $^1$H-NMR*): 7.05–7.35 |
| 28 | 4-Cl-C₆H₄-CH₂-C(CH₃)₂- | H | $CH_3-(CH_2)_3-$ | O | $^1$H-NMR*): 7.05–7.3 |
| 29 | 4-Cl-C₆H₄-CH₂-C(CH₃)₂- | H | $CH_3-(CH_2)_5-$ | O | $^1$H-NMR*): 7.05–7.3 |

-continued

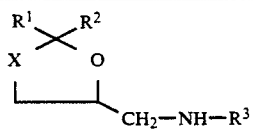

(I)

| Example No. | R¹ | R² | R³ | X | physical properties |
|---|---|---|---|---|---|
| 30 | 4-Cl-C₆H₄-CH₂-C(CH₃)₂- | H | cyclopentyl | O | $^1$H-NMR*): 7.02–7.28 |
| 31 | 4-Cl-C₆H₄-CH₂-C(CH₃)₂- | H | cyclohexyl | O | $^1$H-NMR*): 7.05–7.32 |
| 32 | 4-cyclohexylphenyl | CH₃ | CH₃ | O | $^1$H-NMR*): 7.1–7.4 |
| 33 | 4-cyclohexylphenyl | CH₃ | C₂H₅ | O | $^1$H-NMR*): 7.1–7.45 |
| 34 | 4-cyclohexylphenyl | CH₃ | cyclopentyl | O | $^1$H-NMR*): 7.1–7.45 |
| 35 | 4-cyclohexylphenyl | CH₃ | cyclohexyl | O | $^1$H-NMR*): 7.1–7.4 |
| 36 | 4-cyclohexylphenyl | CH₃ | CH₃—(CH₂)₃— | O | $^1$H-NMR*): 7.1–7.4 |
| 37 | 4-cyclohexylphenyl | CH₃ | (CH₃)₂CH— | O | $^1$H-NMR*): 7.1–7.45 |
| 38 | 4-cyclohexylphenyl | CH₃ | (CH₃)₂CH—CH₂— | O | $^1$H-NMR*): 7.08–7.4 |
| 39 | 4-cyclohexylphenyl | CH₃ | CH₃—(CH₂)₅— | O | $^1$H-NMR*): 7.1–7.4 |
| 40 | 4-biphenylyl | CH₃ | CH₃ | O | $^1$H-NMR*): 7.28–7.65 |
| 41 | 4-biphenylyl | CH₃ | C₂H₅ | O | $^1$H-NMR*): 7.28–7.6 |

-continued $$\begin{array}{c} R^1 \quad R^2 \\ X \quad \diagdown \diagup \quad O \\ \diagdown \diagup \\ CH_2-NH-R^3 \end{array} \quad (I)$$

| Example No. | R¹ | R² | R³ | X | physical properties |
|---|---|---|---|---|---|
| 42 | biphenyl-4-yl | CH₃ | cyclopentyl (H) | O | ¹H-NMR*): 7.3–7.6 |
| 43 | biphenyl-4-yl | CH₃ | cyclohexyl (H) | O | ¹H-NMR*): 7.28, 7.6 |
| 44 | biphenyl-4-yl | CH₃ | CH₃—(CH₂)₃— | O | ¹H-NMR*): 7.28–7.6 |
| 45 | biphenyl-4-yl | CH₃ | (CH₃)₂CH— | O | ¹H-NMR*): 7.25–7.6 |
| 46 | biphenyl-4-yl | CH₃ | (CH₃)₂CH—CH₂— | O | ¹H-NMR*): 7.28–7.62 |
| 47 | biphenyl-4-yl | CH₃ | CH₃—(CH₂)₅— | O | ¹H-NMR*): 7.28–7.6 |
| 48 | 4-Cl-C₆H₄-CH₂-C(CH₃)₂-CH₃ (4-chlorophenyl-neopentyl) | CH₃ | CH₃ | O | $n_D^{20}$ 1.5190 |
| 49 | 4-CH₃-cyclohexyl-CH₂-CH(CH₃)— | CH₃ | CH₃—(CH₂)₂— | O | $n_D^{20}$ 1.4659 |
| 50 | 4-CH₃-C₆H₄-CH₂-CH(CH₃)— | CH₃ | CH₃ | O | $n_D^{20}$ 1.5064 |
| 51 | 4-CH₃-C₆H₄-CH₂-CH(CH₃)— | CH₃ | C₂H₅ | O | $n_D^{20}$ 1.5015 |
| 52 | 4-CH₃-C₆H₄-CH₂-CH(CH₃)— | CH₃ | CH₃—(CH₂)₃— | O | ¹H-NMR*): 2.7; 3.1 |
| 53 | 4-CH₃-C₆H₄-CH₂-CH(CH₃)— | CH₃ | (CH₃)₂CH—CH₂— | O | $n_D^{20}$ 1.4914 |

-continued $$\begin{array}{c} R^1\phantom{X}R^2 \\ X-\underset{O}{\overset{|}{C}}- \\ \phantom{XX}CH_2-NH-R^3 \end{array} \quad (I)$$

| Example No. | R¹ | R² | R³ | X | physical properties |
|---|---|---|---|---|---|
| 54 | 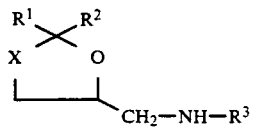 | H | $CH_3-(CH_2)_2-$ | O | $^1$H-NMR*): 2.6; 2.85 |
| 55 | 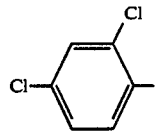 | $CH_3$ | $CH_3$ | O | $n_D^{20}$ 1.4663 |
| 56 | 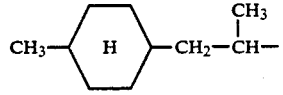 | $CH_3$ | $CH_3-(CH_2)_3-$ | O | $n_D^{20}$ 1.4664 |
| 57 | 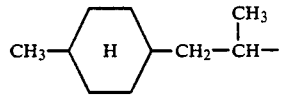 | $CH_3$ | $(CH_3)_2CH-CH_2-$ | O | $^1$H-NMR*): 2.43; 2.78 |
| 58 | 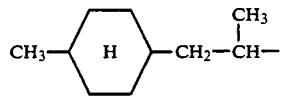 | $CH_3$ | $CH_3$ | O | $^1$H-NMR*): 2.5; 2.7 |
| 59 | 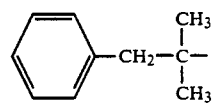 | $CH_3$ | $C_2H_5$ | O | $n_D^{20}$ 1.5097 |
| 60 | 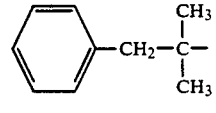 | $CH_3$ | $CH_3-(CH_2)_2-$ | O | $n_D^{20}$ 1.5010 |
| 61 | 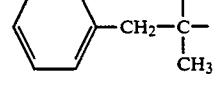 | $CH_3$ | $(CH_3)_2CH-CH_2-$ | O | $n_D^{20}$ 1.4944 |
| 62 | 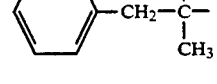 | $CH_3$ | $CH_3-(CH_2)_3-$ | O | $^1$H-NMR*): 2.5; 2.7 |
| 63 | 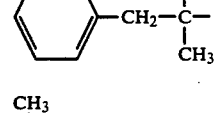 | $CH_3$ | $(CH_3)_2CH-CH_2-$ | O | $^1$H-NMR*): 2.45; 2.65 |
| 64 | 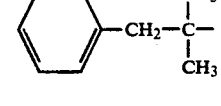 | $CH_3$ | $C_2H_5$ | O | $^1$H-NMR*): 2.7; 2.75 |

-continued

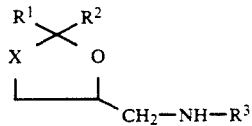
(I)

| Example No. | R¹ | R² | R³ | X | physical properties |
|---|---|---|---|---|---|
| 65 | CH₃ / 3-(CH₃)₃C-CH₂-phenyl | CH₃ | CH₂-(CH₂)₂- | O | $^1$H-NMR*): 2.65; 2.8 |
| 66 | CH₃ / 3-(CH₃)₃C-CH₂-phenyl | CH₃ | CH₃ | O | $n_D^{20}$ 1.5098 |
| 67 | CH₃ / 3-(CH₃)₃C-CH₂-phenyl | CH₃ | CH₃-(CH₂)₃- | O | $n_D^{20}$ 1.4978 |
| 68 | 4-Cl-phenyl-CH₂-CH(CH₃)- | CH₃ | CH₃-(CH₂)₂- | O | $n_D^{20}$ 1.5079 |
| 69 | 4-Cl-phenyl-CH₂-CH(CH₃)- | CH₃ | CH₃-(CH₂)₃- | O | $^1$H-NMR*): 2.65; 2.8 |
| 70 | 4-Cl-phenyl-CH₂-CH(CH₃)- | CH₃ | (CH₃)₂CH-CH₂- | O | $n_D^{20}$ 1.5028 |
| 71 | 4-Cl-phenyl-CH₂-C(CH₃)₂- | CH₃ | (CH₃)₂CH-CH₂- | O | $n_D^{20}$ 1.5063 |
| 72 | CH₃ / 3-(CH₃)₃C-CH₂-cyclohexyl | CH₃ | CH₃-(CH₂)₂- | O | $^1$H-NMR*): 2.6; 2.7 |
| 73 | CH₃ / 3-(CH₃)₃C-CH₂-cyclohexyl | CH₃ | CH₃-(CH₂)₃- | O | $^1$H-NMR*): 2.6; 2.72 |
| 74 | cyclohexyl-CH₂-C(CH₃)₂- | CH₃ | C₂H₅ | O | $n_D^{20}$ 1.4717 |
| 75 | cyclohexyl-CH₂-C(CH₃)₂- | CH₃ | (CH₃)₂CH-CH₂- | O | $n_D^{20}$ 1.4709 |

-continued

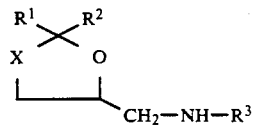

| Example No. | R¹ | R² | R³ | X | physical properties |
|---|---|---|---|---|---|
| 76 | 4-Cl-C₆H₄-CH₂-C(CH₃)₂- | CH₃ | CH₃-(CH₂)₃- | O | ¹H-NMR*): 2.62; 2.75 |
| 77 | 4-Cl-C₆H₄-CH₂-CH(CH₃)- | CH₃ | C₂H₅ | O | $n_D^{20}$ 1.5120 |
| 78 | 3-CH₃-cyclohexyl-CH₂-C(CH₃)₂- | CH₃ | CH₃ | O | $n_D^{20}$ 1.4724 |
| 79 | 4-Cl-C₆H₄-CH₂-C(CH₃)₂- | CH₃ | C₂H₅ | O | ¹H-NMR*): 2.65; 2.8 |
| 80 | 4-Cl-C₆H₄-CH₂-C(CH₃)₂- | CH₃ | CH₃-(CH₂)₂- | O | ¹H-NMR*): 2.65; 2.75 |
| 81 | cyclohexyl-CH₂-C(CH₃)₂- | CH₃ | CH₃(CH₂)₂- | O | ¹H-NMR*): 2.65; 2.75 |
| 82 | cyclohexyl-CH₂-C(CH₃)₂- | CH₃ | CH₃-(CH₂)₃- | O | ¹H-NMR*): 2.70; 2.78 |
| 83 | 4-Cl-C₆H₄-CH₂-CH(CH₃)- | CH₃ | CH₃ | O | $n_D^{20}$ 1.1.5171 |
| 84 | 3-CH₃-cyclohexyl-CH₂-C(CH₃)₂- | CH₃ | C₂H₅ | O | ¹H-NMR*): 2.7 |
| 85 | 3-CH₃-cyclohexyl-CH₂-C(CH₃)₂- | CH₃ | (CH₃)₂CH-CH₂- | O | $n_D^{20}$ 1.4682 |
| 86 | C₆H₅-CH₂-C(CH₃)₂- | CH₃ | cyclopentyl | O | $n_D^{20}$ 1.5143 |

-continued $$\underset{CH_2-NH-R^3}{\overset{R^1\quad R^2}{\underset{|\quad|}{X-C-O}}}\quad(I)$$

| Example No. | R¹ | R² | R³ | X | physical properties |
|---|---|---|---|---|---|
| 87 | 3,4,5-trichlorophenyl | H | CH$_3$—(CH$_2$)$_2$— | O | n$_D^{20}$ 1.5424 |
| 88 | 2,4-dichlorophenyl | H | C$_2$H$_5$ | O | $^1$H-NMR*): 2.6; 2.85 |
| 89 | 2,4-dichlorophenyl | H | CH$_3$—(CH$_2$)$_3$— | O | $^1$H-NMR*): 2.65; 2.85 |
| 90 | 2,4-dichlorophenyl | H | (CH$_3$)$_2$CH—CH$_2$— | O | $^1$H-NMR*): 2.45; 2.85 |
| 91 | 2,4-dichlorophenyl | H | (CH$_3$)$_3$C— | O | n$_D^{20}$ 1.5236 |
| 92 | 2,4-dichlorophenyl | H | CH$_3$—(CH$_2$)$_4$— | O | n$_D^{20}$ 1.5223 |
| 93 | 2,4-dichlorophenyl | H | CH$_3$—(CH$_2$)$_5$— | O | $^1$H-NMR*): 2.65; 2.85 |
| 94 | 2,4-dichlorophenyl | H | cyclohexyl | O | $^1$H-NMR*): 2.45; 2.9 |
| 95 | 2,4-dichloro-phenyl-O—CH$_2$—C(CH$_3$)$_2$—CH$_3$ | CH$_3$ | CH$_3$—(CH$_2$)$_2$— | O | $^1$H-NMR*): 2.6; 2.75 |

-continued

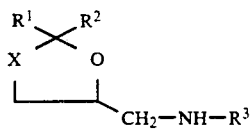
(I)

| Example No. | R¹ | R² | R³ | X | physical properties |
|---|---|---|---|---|---|
| 96 | 2,4-dichlorophenyl-O-CH₂-C(CH₃)₂- | CH₃ | CH₃-(CH₂)₃- | O | $n_D^{20}$ 1.5146 |
| 97 | 2,4-dichlorophenyl-O-CH₂-C(CH₃)₂- | CH₃ | (CH₃)₂CH-CH₂- | O | $n_D^{20}$ 1.5116 |
| 98 | 4-chlorophenyl-O-CH₂-C(CH₃)₂- | CH₃ | CH₃-(CH₂)₂- | O | ¹H-NMR*): 2.6; 2.75 |
| 99 | 4-chlorophenyl-O-CH₂-C(CH₃)₂- | CH₃ | CH₃-(CH₂)₃- | O | $n_D^{20}$ 1.5057 |
| 100 | 4-chlorophenyl-O-CH₂-C(CH₃)₂- | CH₃ | (CH₃)₂CH-CH₂- | O | $n_D^{20}$ 1.5019 |
| 101 | 3-chlorophenyl-CH₂-C(CH₃)₂- | CH₃ | CH₃-(CH₂)₂- | O | ¹H-NMR*): 2.6; 2.75 |
| 102 | 3-chlorophenyl-CH₂-C(CH₃)₂- | CH₃ | CH₃-(CH₂)₃- | O | $n_D^{20}$ 1.5093 |
| 103 | 3-chlorophenyl-CH₂-C(CH₃)₂- | CH₃ | (CH₃)₂CH-CH₂- | O | $n_D^{20}$ 1.5074 |
| 104 | 3-chlorophenyl-CH₂-C(CH₃)₂- | CH₃ | CH₃ | O | $n_D^{20}$ 1.5199 |
| 105 | 4-chlorophenyl-O-CH₂-C(CH₃)₂- | CH₃ | CH₃ | O | $n_D^{20}$ 1.5151 |

-continued

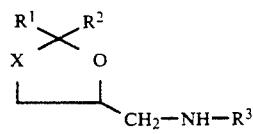
(I)

| Example No. | R¹ | R² | R³ | X | physical properties |
|---|---|---|---|---|---|
| 106 | 2,4-dichlorophenyl-O-CH₂-C(CH₃)₂-CH₃ | CH₃ | CH₃ | O | ¹H-NMR*): 2.48; 2.7 |
| 107 | 3-chlorophenyl-CH₂-C(CH₃)₂-CH₃ | CH₃ | C₂H₅ | O | $n_D^{20}$ 1.5156 |
| 108 | 4-chlorophenyl-O-CH₂-C(CH₃)₂-CH₃ | CH₃ | C₂H₅ | O | ¹H-NMR*): 2.7; 2.78 |
| 109 | 2,4-dichlorophenyl-O-CH₂-C(CH₃)₂-CH₃ | CH₃ | C₂H₅ | O | ¹H-NMR*): 2.6; 2.7 |
| 110 | trichlorophenyl | H | CH₃—(CH₂)₃— | O | ¹H-NMR*): 2.65; 2.85 |
| 111 | trichlorophenyl | H | (CH₃)₂CH—CH₂— | O | $n_D^{20}$ 1.5320 |
| 112 | trichlorophenyl | H | CH₃ | O | ¹H-NMR*): 2.5; 2.85 |
| 113 | trichlorophenyl | H | C₂H₅ | O | $n_D^{20}$ 1.5502 |
| 114 | 3-methylphenyl-CH₂-C(CH₃)₂-CH₃ | CH₃ | cyclopentyl | O | $n_D^{20}$ 1.5143 |

-continued $$\begin{array}{c} R^1 \quad R^2 \\ X \diagdown \diagup O \\ | \\ CH_2-NH-R^3 \end{array} \qquad (I)$$

| Example No. | R¹ | R² | R³ | X | physical properties |
|---|---|---|---|---|---|
| 115 | 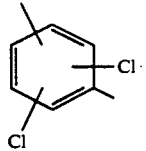 (trichlorophenyl) | H | $CH_3-(CH_2)_5-$ | O | $n_D^{20}$ 1.5230 |
| 116 | 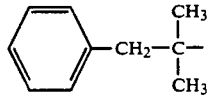 (PhCH₂C(CH₃)₂–) | $CH_3$ | 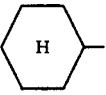 (cyclohexyl) | O | ¹H-NMR*): 2.45; 2.75 |
| 117 | 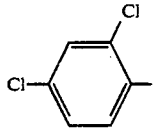 (dichlorophenyl) | H | $CH_3-(CH_2)_5-$ | O | $n_D^{20}$ 1.5142 |
| 118 | 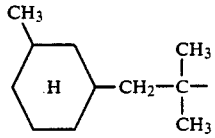 (methylcyclohexyl-CH₂C(CH₃)₂–) | $CH_3$ |  (cyclopentyl) | O | $n_D^{20}$ 1.4830 |
| 119 | 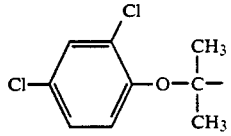 (dichlorophenoxy-C(CH₃)₂–) | $CH_3$ | $CH_3-CH-CH_2-$<br>　　　　$\mid$<br>　　　　$OH$ | O | $n_D^{20}$ 1.5297 |
| 120 | 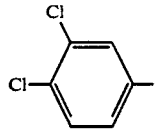 (dichlorophenyl) | H | $(CH_3)_2CH-CH_2-$ | O | $n_D^{20}$ 1.5237 |
| 121 | 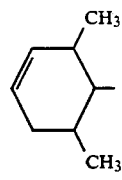 (trimethylcyclohexenyl) | H | $CH_3-(CH_2)_3-$ | O | $n_D^{20}$ 1.4781 |
| 122 | 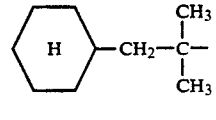 (cyclohexyl-CH₂C(CH₃)₂–) | $CH_3$ | 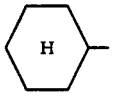 (cyclohexyl) | O | $n_D^{20}$ 1.4854 |
| 123 | 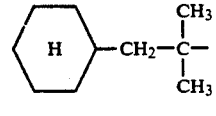 (cyclohexyl-CH₂C(CH₃)₂–) | $CH_3$ |  (cyclopentyl) | O | ¹H-NMR*): 2.7; 3.1 |
| 124 | 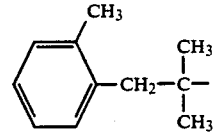 (methylphenyl-CH₂C(CH₃)₂–) | $CH_3$ | $(CH_3)_2CH-CH_2-$ | O | $n_D^{20}$ 1.4978 |

-continued

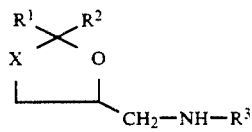
(I)

| Example No. | R¹ | R² | R³ | X | physical properties |
|---|---|---|---|---|---|
| 125 | 2-(neopentyl)tolyl (CH₃ ortho, CH₂-C(CH₃)₃) | CH₃ | CH₃—(CH₂)₃— | O | $n_D^{20}$ 1.5008 |
| 126 | 2-(neopentyl)tolyl | CH₃ | (CH₃)₂CH— | O | $n_D^{20}$ 1.5029 |
| 127 | 2-(neopentyl)methylcyclohexyl | CH₃ | (CH₃)₂CH—CH₂— | O | $n_D^{20}$ 1.4700 |
| 128 | 2-(neopentyl)methylcyclohexyl | CH₃ | CH₃—(CH₂)₃— | O | ¹H-NMR*): 2.65; 2.75 |
| 129 | 2-(neopentyl)methylcyclohexyl | CH₃ | (CH₃)₂CH— | O | $n_D^{20}$ 1.4709 |
| 130 | neopentylphenyl | CH₃ | (CH₃)₃C— | O | $n_D^{20}$ 1.4958 |
| 131 | 4-methylphenyl-CH₂-CH(C₂H₅)- | CH₃ | (CH₃)₃C— | O | $n_D^{20}$ 1.4941 |
| 132 | phenyl-CH₂-CH(CH₃)- | CH₃ | (CH₃)₃C— | O | $n_D^{20}$ 1.4925 |
| 133 | 2-(neopentyl)tolyl | CH₃ | (CH₃)₃C— | O | $n_D^{20}$ 1.4977 |
| 134 | 3-chloro-(neopentyl)phenyl | CH₃ | (CH₃)₃C— | O | $n_D^{20}$ 1.5035 |

-continued

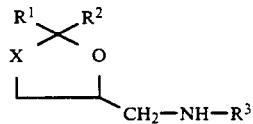

(I)

| Example No. | R¹ | R² | R³ | X | physical properties |
|---|---|---|---|---|---|
| 135 | 4-F-C₆H₄-CH₂-CH(CH₃)- | CH₃ | (CH₃)₃C- | O | $n_D^{20}$ 1.4840 |
| 136 | 3-Cl-C₆H₄-CH₂-CH(C₂H₅)- | CH₃ | (CH₃)₃C- | O | $n_D^{20}$ 1.5025 |
| 137 | 3-F-C₆H₄-CH₂-C(CH₃)₂- | CH₃ | (CH₃)₃C- | O | $n_D^{20}$ 1.4888 |
| 138 | 3-Cl-C₆H₄-CH₂-CH(CH₃)- | CH₃ | (CH₃)₃C- | O | $n_D^{20}$ 1.5036 |
| 139 | 4-Cl-C₆H₄-CH₂-CH(C₂H₅)- | CH₃ | (CH₃)₃C- | O | $n_D^{20}$ 1.5009 |
| 140 | 4-Cl-C₆H₄-CH₂-CH(CH₃)- | CH₃ | (CH₃)₃C- | O | $n_D^{20}$ 1.5026 |
| 141 | 4-Cl-C₆H₄-CH₂-C(CH₃)₂- | CH₃ | (CH₃)₃C- | O | $n_D^{20}$ 1.5054 |
| 142 | C₆H₁₁-CH₂-C(CH₃)₂- | CH₃ | (CH₃)₃C- | O | ¹H-NMR*): 2.6 |
| 143 | 4-CH₃-C₆H₁₀-CH₂-CH(C₂H₅)- | CH₃ | (CH₃)₃C- | O | $n_D^{20}$ 1.4645 |
| 144 | C₆H₁₁-CH₂-CH(CH₃)- | CH₃ | (CH₃)₃C- | O | $n_D^{20}$ 1.4638 |
| 145 | 2-CH₃-C₆H₁₀-CH₂-C(CH₃)₂- | CH₃ | (CH₃)₃C- | O | $n_D^{20}$ 1.4698 |

-continued

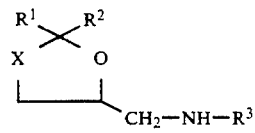
(I)

| Example No. | R¹ | R² | R³ | X | physical properties |
|---|---|---|---|---|---|
| 146 | 2-Cl-C₆H₄-CH₂-CH(C₂H₅)- | CH₃ | (CH₃)₃C— | O | $n_D^{20}$ 1.5015 |
| 147 | 4-(CH₃)₃O-C₆H₄- | H | CH₃—(CH₂)₃— | O | $n_D^{20}$ 1.4996 |
| 148 | 3-CF₃-C₆H₄-CH₂-CH(CH₃)- | CH₃ | CH₃—(CH₂)₃— | O | $n_D^{20}$ 1.4667 |
| 149 | 4-(CH₃)₃C-C₆H₄- | H | CH₃—(CH₂)₂— | O | $n_D^{20}$ 1.5035 |
| 150 | 4-(CH₃)₃C-C₆H₁₀- | H | CH₃—(CH₂)₃— | O | $n_D^{20}$ 1.4701 |
| 151 | 3-CH₃-C₆H₁₀-CH₂-C(CH₃)₂-CH₃ | CH₃ | (CH₃)₃C— | O | $n_D^{20}$ 1.4663 |
| 152 | 4-(CH₃)₃C-C₆H₄-CH₂-CH(CH₃)- | H | CH₃—(CH₂)₂—CH(CH₃)— / CH₃—(CH₂)₄— (60:40) | O | $n_D^{20}$ 1.4926 |
| 153 | 4-(CH₃)₃C-C₆H₄-CH₂-CH(CH₃)- | H | CH₃—(CH₂)₅— | O | $n_D^{20}$ 1.4918 |
| 154 | 4-CH₃-C₆H₁₀-CH₂-CH(CH₃)- | CH₃ | (CH₃)₃C— | O | ¹H-NMR*): 2.6 |
| 155 | 2-CH₃-C₆H₁₀-CH₂-CH(CH₃)- | CH₃ | (CH₃)₃C— | O | $n_D^{20}$ 1.4658 |
| 156 | 3-CH₃-C₆H₁₀-CH₂-CH(CH₃)- | CH₃ | (CH₃)₃C— | O | ¹H-NMR*): 2.78 |

-continued $$\text{(I)}$$

| Example No. | R¹ | R² | R³ | X | physical properties |
|---|---|---|---|---|---|
| 157 | CF₃ / H cyclohexyl with -CH₂-CH(CH₃)- | CH₃ | CH₃—(CH₂)₃— | O | $n_D^{20}$ 1.4449 |
| 158 | (CH₃)₃C- cyclohexyl -H | H | CH₃—(CH₂)₂— | O | $n_D^{20}$ 1.4702 |
| 159 | (CH₃)₃C—C₆H₄—CH₂—CH(CH₃)— | H | CH₃—(CH₂)₂— | O | $n_D^{20}$ 1.4971 |
| 160 | (CH₃)₃C—C₆H₄—CH₂—CH(CH₃)— | H | (CH₃)₂CH—CH₂— | O | $n_D^{20}$ 1.4924 |
| 161 | (CH₃)₃C—C₆H₄—CH₂—CH(CH₃)— | H | CH₃ | O | $n_D^{20}$ 1.5036 |
| 162 | (CH₃)₃C—C₆H₄—CH₂—CH(CH₃)— | H | CH₃—(CH₂)₃— | O | $n_D^{20}$ 1.4954 |
| 163 | (CH₃)₃C—C₆H₄—CH₂—CH(CH₃)— | H | (CH₃)₃C— | O | $n_D^{20}$ 1.4917 |
| 164 | Cl—C₆H₄—O—CH₂—C(CH₃)₂— | CH₃ | (CH₃)₃C— | O | ¹H-NMR[*]: 2.7 |
| 165 | (CH₃)₃C—C₆H₄—CH₂—CH(CH₃)— | H | C₂H₅ | O | $n_D^{20}$ 1.5002 |
| 166 | C₆H₅—CH₂—CH₂— | CH₃ | CH₃—(CH₂)₂— | O | $n_D^{20}$ 1.4962 |
| 167 | C₆H₅—CH₂—CH₂— | CH₃ | CH₃—(CH₂)₃— | O | $n_D^{20}$ 1.4934 |
| 168 | (CH₃)₃C- cyclohexyl -H, -CH₂—CH(CH₃)— | H | CH₃ | O | $n_D^{20}$ 1.4741 |

-continued

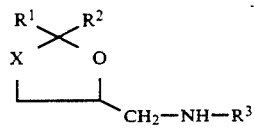
(I)

| Example No. | R¹ | R² | R³ | X | physical properties |
|---|---|---|---|---|---|
| 169 | (CH₃)₃C—[cyclohexyl-H]—CH₂—CH(CH₃)— | H | $C_2H_5$ | O | $n_D^{20}$ 1.4711 |
| 170 | (CH₃)₃C—[cyclohexyl-H]—CH₂—CH(CH₃)— | H | $CH_3-(CH_2)_2-$ | O | $n_D^{20}$ 1.4707 |
| 171 | (CH₃)₃C—[cyclohexyl-H]—CH₂—CH(CH₃)— | H | $CH_3-(CH_2)_3-$ | O | $n_D^{20}$ 1.4694 |
| 172 | (CH₃)₃C—[cyclohexyl-H]—CH₂—CH(CH₃)— | H | $(CH_3)_2CH-CH_2-$ | O | $n_D^{20}$ 1.4679 |
| 173 | (CH₃)₃C—[cyclohexyl-H]—CH₂—CH(CH₃)— | H | $(CH_3)_3C-$ | O | $n_D^{20}$ 1.4704 |
| 174 | (CH₃)₃C—[cyclohexyl-H]—CH₂—CH(CH₃)— | H | $CH_3-(CH_2)_2-CH(CH_3)-$ / $CH_3(CH_2)_4-$ (60:40) | O | $n_D^{20}$ 1.4687 |
| 175 | (CH₃)₃C—[cyclohexyl-H]—CH₂—CH(CH₃)— | H | $CH_3-(CH_2)_5-$ | O | $n_D^{20}$ 1.4685 |
| 176 | [cyclohexyl-H]—CH₂—CH₂— | $CH_3$ | $CH_3-(CH_2)_2-$ | O | $n_D^{20}$ 1.4645 |
| 177 | [cyclohexyl-H]—CH₂—CH₂— | $CH_3$ | $CH_3-(CH_2)_3-$ | O | $n_D^{20}$ 1.4634 |
| 178 | 2-Cl-4-(CF₃O)-phenyl— | H | $CH_3-(CH_2)_2-CH(CH_3)-$ / $CH_3-(CH_2)_4-$ (60:40) | O | $n_D^{20}$ 1.4715 |
| 179 | 2-Cl-4-(CF₃O)-phenyl— | H | $CH_3-(CH_2)_5-$ | O | $n_D^{20}$ 1.4720 |

-continued

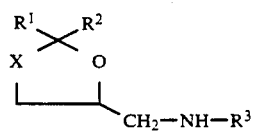
(I)

| Example No. | R¹ | R² | R³ | X | physical properties |
|---|---|---|---|---|---|
| 180 | 3-Cl, 4-CF₃O-phenyl | H | cyclopentyl | O | $n_D^{20}$ 1.4886 |
| 181 | 3-Cl, 4-CF₃O-phenyl | H | cyclohexyl | O | $n_D^{20}$ 1.4905 |
| 182 | 3-Cl, 4-CF₃O-phenyl | H | CH₃—(CH₂)₃— | O | $n_D^{20}$ 1.4788 |
| 183 | 3-Cl, 4-CF₃O-phenyl | H | (CH₃)₂CH—CH₂— | O | $n_D^{20}$ 1.4730 |
| 184 | 3-Cl, 4-CF₃O-phenyl | H | (CH₃)₃C— | O | ¹H-NMR*): 2.83 |
| 185 | 3-Cl, 4-CF₃O-phenyl | H | CH₃—(CH₂)₂— | O | $n_D^{20}$ 1.4750 |
| 186 | 3-Cl, 4-CF₃O-phenyl | H | C₂H₅ | O | ¹H-NMR*): 2.75; 2.88 |
| 187 | 2,4-dichlorophenyl | H | CH₂=CH—CH₂— | O | $n_D^{20}$ 1.5411 |
| 188 | 4-(CH₃)₃C-phenyl-CH₂-CH(CH₃)— | H | cyclopentyl | O | $n_D^{20}$ 1.5096 |
| 189 | 4-(CH₃)₃C-phenyl-CH₂-CH(CH₃)— | H | cyclohexyl | O | $n_D^{20}$ 1.5096 |

-continued

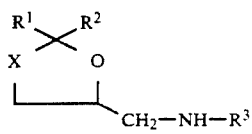

(I)

| Example No. | R¹ | R² | R³ | X | physical properties |
|---|---|---|---|---|---|
| 190 | 4-Cl-C₆H₄-O-CH₂-C(CH₃)₂- | CH₃ | cyclohexyl (H) | O | $n_D^{20}$ 1.5184 |
| 191 | 2-Cl-4-(F₃C)-C₆H₃- | H | CH₃-(CH₂)₂- | O | ¹H-NMR*): 2.6; 2.9 |
| 192 | 2-Cl-4-(F₃C)-C₆H₃- | H | cyclopentyl (H) | O | $n_D^{20}$ 1.4950 |
| 193 | 2-Cl-4-(F₃C)-C₆H₃- | H | cyclohexyl (H) | O | $n_D^{20}$ 1.5942 |
| 194 | 2-Cl-4-(F₃C)-C₆H₃- | H | C₂H₅ | O | $n_D^{20}$ 1.4842 |
| 195 | 4-(CH₃)₃C-C₆H₁₀(H)-CH₂-CH(CH₃)- | H | cyclopentyl (H) | O | $n_D^{20}$ 1.4823 |
| 196 | 4-(CH₃)₃C-C₆H₁₀(H)-CH₂-CH(CH₃)- | H | cyclohexyl (H) | O | ¹H-NMR*): 2.45; 2.7 |
| 197 | 2,4-Cl₂-C₆H₃-O-CH₂-C(CH₃)₂- | CH₃ | cyclohexyl (H) | O | $n_D^{20}$ 1.5260 |
| 198 | C₆H₅-CH₂-C(CH₃)₂- | CH₃ | 2-CH₃-cyclohexyl (H) | O | $n_D^{20}$ 1.5142 |
| 199 | C₆H₅-CH₂-C(CH₃)₂- | CH₃ | 4-CH₃-cyclohexyl (H) | O | $n_D^{20}$ 1.5069 |

-continued

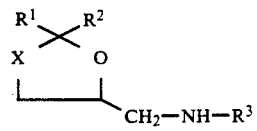

(I)

| Example No. | R¹ | R² | R³ | X | physical properties |
|---|---|---|---|---|---|
| 200 | C₆H₅—CH₂—C(CH₃)₂— | CH₃ | 4-CH₃-cyclohexyl | O | $n_D^{20}$ 1.5062 |
| 201 | C₆H₅—CH₂—C(CH₃)₂— | CH₃ | 3,3,5-tri(CH₃)-cyclohexyl | O | $n_D^{20}$ 1.5041 |
| 202 | C₆H₅—CH₂—C(CH₃)₂— | CH₃ | CH₃O—(CH₂)₂— | O | $n_D^{20}$ 1.5028 |
| 203 | 4-Cl—C₆H₄—O—CH₂—C(CH₃)₂— | CH₃ | CH₃ | O | B.p. 146° C./ 0.01 mbar |
| 204 | 4-Cl—C₆H₄—O—CH₂—C(CH₃)₂— | CH₃ | CH₃ | S | $n_D^{20}$ 1.5361 |
| 205 | 3-CF₃—C₆H₄—O—C(CH₃)₂— | CH₃ | CH₃ | O | B.p. 125° C./ 0.1 mbar |
| 206 | 2,6-di-Cl—C₆H₃— | H | CH₃—(CH₂)₂— | CH₂ | M.p. 43° C. |
| 207 | 2,6-di-Cl—C₆H₃— | H | CH₃—(CH₂)₃— | CH₂ | M.p. 46° C. |
| 208 | 2,6-di-Cl—C₆H₃— | H | CH₃—(CH₂)₅— | CH₂ | $n_D^{20}$ 1.5254 |
| 209 | 2,4-di-Cl—C₆H₃—O—C(CH₃)₂— | CH₃ | (CH₃)₃C— | O | $n_D^{20}$ 1.5090 |

-continued

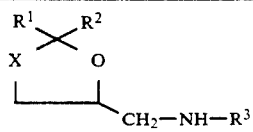
(I)

| Example No. | R¹ | R² | R³ | X | physical properties |
|---|---|---|---|---|---|
| 210 | 3,4-dichlorophenyl-O-C(CH₃)₂- | CH₃ | (C₂H₅)₂CH-CH₂- | O | $n_D^{20}$ 1.5100 |
| 211 | 3,4-dichlorophenyl-O-C(CH₃)₂- | CH₃ | CH₃O—CH₂—CH₂— | O | $n_D^{20}$ 1.5198 |
| 212 | 3,4-dichlorophenyl-O-C(CH₃)₂- | CH₃ | C₂H₅—O—(CH₂)₃— | O | $n_D^{20}$ 1.5131 |
| 213 | 3,4-dichlorophenyl-O-C(CH₃)₂- | CH₃ | CH₃O—CH₂—CH₂— | benzisothiazole-CO-NH-SO₂ | $n_D^{20}$ 1.5420 |
| 214 | 3,4-dichlorophenyl-O-C(CH₃)₂- | CH₃ | C₂H₅O—(CH₂)₃— | benzisothiazole-CO-NH-SO₂ | $n_D^{20}$ 1.5424 |
| 215 | 3,4-dichlorophenyl-O-C(CH₃)₂- | CH₃ | (C₂H₅)₂CH—CH₂— | benzisothiazole-CO-NH-SO₂ | $n_D^{20}$ 1.5448 |
| 216 | 4-(CH₃)₃C-phenyl- | H | (CH₃)₂CH— | CH₂ | $n_D^{20}$ 1.5151 |
| 217 | 4-(CH₃)₃C-phenyl- | H | cyclohexyl- | CH₂ | $n_D^{20}$ 1.5243 |

-continued

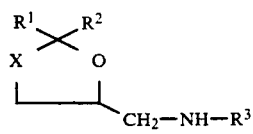
(I)

| Example No. | R¹ | R² | R³ | X | physical properties |
|---|---|---|---|---|---|
| 218 | 4-(CH₃)₃C-C₆H₄- | H | CH₃—(CH₂)₅— | CH₂ | $n_D^{20}$ 1.5038 |
| 219 | 3-CF₃-C₆H₄-O-CH₂-C(CH₃)₂- | CH₃ | CH₃—CH(OH)—CH₂— | O | $n_D^{20}$ 1.4648 |
| 220 | 3-CF₃-C₆H₄-O-CH₂-C(CH₃)₂- | CH₃ | C₂H₅O—(CH₂)₃— | O | $n_D^{20}$ 1.4695 |
| 221 | 3-CF₃-C₆H₄-O-CH₂-C(CH₃)₂- | CH₃ | (CH₃)₂CH—CH₂— | O | $n_D^{20}$ 1.4590 |
| 222 | 3,4-Cl₂-C₆H₃- | H | cyclopentyl | O | $n_D^{20}$ 1.5456 |
| 223 | 3,4-Cl₂-C₆H₃- | H | cyclohexyl | O | ¹H-NMR*): |
| 224 | 3,4-Cl₂-C₆H₃- | H | 2-methylcyclohexyl | O | $n_D^{20}$ 1.5374 |
| 225 | 2-CF₃-C₆H₄-CH₂-C(CH₃)₂- | CH₃ | cyclohexyl | O | $n_D^{20}$ 1.4909 |
| 226 | 3,4-Cl₂-C₆H₃- | H | 3-methylcyclohexyl | O | $n_D^{20}$ 1.5345 |
| 227 | 3,4-Cl₂-C₆H₃- | H | 4-methylcyclohexyl | O | $n_D^{20}$ 1.5323 |

-continued

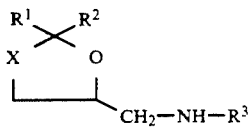
(I)

| Example No. | R¹ | R² | R³ | X | physical properties |
|---|---|---|---|---|---|
| 228 | 3,4-dichlorophenyl | H | 3,3,5-trimethylcyclohexyl | O | $n_D^{20}$ 1.5267 |
| 229 | 3,4-dichlorophenyl | H | $CH_2-CH=CH_2-$ | O | $n_D^{20}$ 1.5440 |
| 230 | cyclohexyl-$CH_2-C(CH_3)_2-$ | $CH_3$ | 2-methylcyclohexyl | O | $n_D^{20}$ 1.4846 |
| 231 | cyclohexyl-$CH_2-C(CH_3)_2-$ | $CH_3$ | 3-methylcyclohexyl | O | $n_D^{20}$ 1.4836 |
| 232 | cyclohexyl-$CH_2-C(CH_3)_2-$ | $CH_3$ | 4-methylcyclohexyl | O | $n_D^{20}$ 1.4836 |
| 233 | cyclohexyl-$CH_2-C(CH_3)_2-$ | $CH_3$ | $CH_3O-CH_2-CH_2-$ | O | $n_D^{20}$ 1.4714 |
| 234 | 2-($CF_3$)cyclohexyl-$CH_2-C(CH_3)_2-$ | $CH_3$ | cyclohexyl | O | ¹H-NMR*): |
| 235 | cyclohexyl-$CH_2-C(CH_3)_2-$ | $CH_3$ | 3,3,5-trimethylcyclohexyl | O | $n_D^{20}$ 1.4824 |
| 236 | 2,4-dichlorophenyl-$O-C(CH_3)_2-$ | $CH_3$ | $-CH_2-CH_2-OCH_3$ | O | $n_D^{20}$ 1.5178 |
| 237 | 3-methylphenyl-$CH_2-C(CH_3)_2-$ | $CH_3$ | $-CH_2-$(2-furyl) | O | $n_D^{20}$ 1.5266 |

-continued

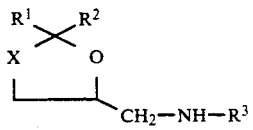
(I)

| Example No. | R[1] | R[2] | R[3] | X | physical properties |
|---|---|---|---|---|---|
| 238 | 3-(F₃C)-C₆H₄-CH₂-C(CH₃)₂- | CH₃ | cyclohexyl | O | $n_D^{20}$ 1.4849 |
| 239 | 4-(F₃C)-C₆H₄-CH₂-C(CH₃)₂- | CH₃ | cyclohexyl | O | $n_D^{20}$ 1.4860 |
| 240 | 4-CH₃-cyclohexyl-CH₂-C(CH₃)₂- | CH₃ | -CH₂-tetrahydrofuran-2-yl | O | $n_D^{20}$ 1.4803 |
| 241 | C₆H₅-CH₂-C(CH₃)₂- | CH₃ | cyclopentyl | O (X = saccharinyl: benzo[d]isothiazol-3(2H)-one 1,1-dioxide) | |
| 242 | 3-CH₃-C₆H₄-CH₂-C(CH₃)₂- | CH₃ | 4-methylcyclohexyl | O | $n_D^{20}$ 1.5090 |
| 243 | 3-CH₃-C₆H₄-CH₂-C(CH₃)₂- | CH₃ | 4-methylcyclohexyl | O | $n_D^{20}$ 1.5080 |
| 244 | 3-CH₃-C₆H₄-CH₂-C(CH₃)₂- | CH₃ | 3,3,5-trimethylcyclohexyl | O | $n_D^{20}$ 1.5056 |
| 245 | 4-(F₃C)-cyclohexyl-CH₂-C(CH₃)₂- | CH₃ | cyclohexyl | O | $n_D^{20}$ 1.4631 |
| 246 | 4-(F₃C)-cyclohexyl-CH₂-C(CH₃)₂- | CH₃ | cyclohexyl | O | $n_D^{20}$ 1.4644 |

-continued

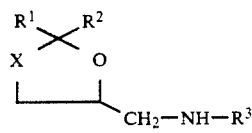

(I)

| Example No. | R¹ | R² | R³ | X | physical properties |
|---|---|---|---|---|---|
| 247 | 1-CH₃, 3-CH₂-C(CH₃)₂-CH₃ cyclohexyl (H) | CH₃ | 4-CH₃-cyclohexyl (H) | O | $n_D^{20}$ 1.4814 |
| 248 | 1-CH₃, 3-CH₂-C(CH₃)₂-CH₃ cyclohexyl (H) | CH₃ | 4-CH₃-cyclohexyl (H) | O | $n_D^{20}$ 1.4807 |
| 249 | 3-CH₃, 1-CH₂-C(CH₃)₂-CH₃ phenyl | CH₃ | -CH₂-CH(C₂H₅)((CH₂)₃-CH₃) | O | $n_D^{20}$ 1.4916 |
| 250 | 3-CH₃, 1-CH₂-C(CH₃)₂-CH₃ phenyl | CH₃ | -CH₂-CH(C₂H₅)(C₂H₅) | O | $n_D^{20}$ 1.4960 |
| 251 | 3-CH₃, 1-CH₂-C(CH₃)₂-CH₃ phenyl | CH₃ | -(CH₂)₃-OC₂H₅ | O | $n_D^{20}$ 1.4980 |
| 252 | 3-CH₃, 1-CH₂-C(CH₃)₂-CH₃ phenyl | CH₃ | -(CH₂)₃-O-(CH₂)₃-CH₃ | O | $n_D^{20}$ 1.4904 |
| 253 | 3-CH₃, 1-CH₂-C(CH₃)₂-CH₃ phenyl | CH₃ | -(CH₂)₂-OCH₃ | O | $n_D^{20}$ 1.5026 |
| 254 | 1-CH₃, 3-CH₂-C(CH₃)₂-CH₃ cyclohexyl (H) | CH₃ | 3,3,5-tri-CH₃-cyclohexyl (H) | O | $n_D^{20}$ 1.4809 |
| 255 | 1-CH₃, 3-CH₂-C(CH₃)₂-CH₃ cyclohexyl (H) | CH₃ | -CH₂-CH(C₂H₅)((CH₂)₃-CH₃) | O | $n_D^{20}$ 1.4683 |

-continued

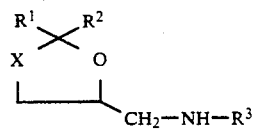
(I)

| Example No. | R¹ | R² | R³ | X | physical properties |
|---|---|---|---|---|---|
| 256 | 3-methylcyclohexyl-CH₂-C(CH₃)₂- | CH₃ | -CH₂-CH(C₂H₅)₂ | O | |
| 257 | 3-methylcyclohexyl-CH₂-C(CH₃)₂- | CH₃ | -(CH₂)₃-OC₂H₅ | O | $n_D^{20}$ 1.4693 |
| 258 | 3-methylcyclohexyl-CH₂-C(CH₃)₂- | CH₃ | 2-methylcyclohexyl | O | $n_D^{20}$ 1.4826 |
| 259 | 3-methylcyclohexyl-CH₂-C(CH₃)₂- | CH₃ | -(CH₂)₃-O-(CH₂)₃-CH₃ | O | $n_D^{20}$ 1.4667 |
| 260 | 3-methylcyclohexyl-CH₂-C(CH₃)₂- | CH₃ | -(CH₂)₂-OCH₃ | O | $n_D^{20}$ 1.4690 |
| 261 | CH₃-(CH₂)₂-O-[3-substituted phenyl]-CH₂-CH(CH₃)- | CH₃ | cyclohexyl | O | $n_D^{20}$ 1.5094 |
| 262 | CH₃-(CH₂)₃-O-[3-substituted phenyl]-CH₂-CH(CH₃)- | CH₃ | cyclohexyl | O | $n_D^{20}$ 1.5072 |
| 263 | CH₃-(CH₂)₃-O-[3-substituted phenyl]-CH₂-CH(CH₃)- | CH₃ | -(CH₃)₃ | O | $n_D^{20}$ 1.4944 |
| 264 | CH₃-(CH₂)₂-O-[3-substituted phenyl]-CH₂-CH(CH₃)- | CH₃ | -C(CH₃)₃ | O | $n_D^{20}$ 1.4944 |
| 265 | (CH₃)₃C-[4-substituted phenyl]- | CH₃ | -CH₂-CH(C₂H₅)₂ | -CH₂- | $n_D^{20}$ 1.5031 |

-continued

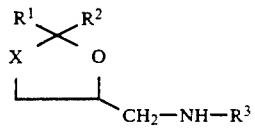
(I)

| Example No. | R¹ | R² | R³ | X | physical properties |
|---|---|---|---|---|---|
| 266 | 4-(CH₃)₃C-C₆H₄- | H | 4-methylcyclohexyl | —CH₂— | $n_D^{20}$ 1.5208 |
| 267 | 2,4-dichloro-5-methylphenyl-S-C(CH₃)₂- | CH₃ | 4-methylcyclohexyl | O | $n_D^{20}$ 1.5310 |
| 268 | 2,4-dichloro-5-methylphenyl-S-C(CH₃)₂- | CH₃ | —(CH₂)₃—OC₂H₅ | O | $n_D^{20}$ 1.5375 |
| 269 | 3,4-dichlorophenyl-S-C(CH₃)₂- | CH₃ | —CH₂-cyclohexyl | O | $n_D^{20}$ 1.5369 |
| 270 | 3,4-dichlorophenyl-O-C(CH₃)₂- | CH₃ | —CH₂-(tetrahydrofuran-2-yl) | O | $n_D^{20}$ 1.5228 |
| 271 | 3,4-dichlorophenyl-O-C(CH₃)₂- | CH₃ | 4-methylcyclohexyl | O | $n_D^{20}$ 1.5211 |
| 272 | CH₃—(CH₂)₃—O-[4-(isobutyl)cyclohexyl]- | CH₃ | cyclohexyl | O | $n_D^{20}$ 1.4777 |
| 273 | CH₃—(CH₂)₂—O-[4-(isobutyl)cyclohexyl]- | CH₃ | cyclohexyl | O | $n_D^{20}$ 1.4773 |
| 274 | 3-chloro-4-(F₃CO)phenyl-O-CH₂-C(CH₃)₂- | CH₃ | 4-methylcyclohexyl | S | $n_D^{20}$ 1.5039 |

-continued $$\begin{array}{c} R^1 \quad R^2 \\ X \diagdown \diagup O \\ | \quad | \\ CH_2-NH-R^3 \end{array} \quad (I)$$

| Example No. | R[1] | R[2] | R[3] | X | physical properties |
|---|---|---|---|---|---|
| 275 | ![Cl, F3CO-phenyl-O-CH2-C(CH3)2-] (3-Cl-4-F3CO-phenoxy-CH2-C(CH3)2-) | CH3 | —CH2—CH(CH3)2 | S | $n_D^{20}$ 1.4942 |
| 276 | (C2H5, Cl-phenyl-O-C(CH3)2-) | CH3 | —CH2—C(CH3)2—CH2—OH | O | $n_D^{20}$ 1.4979 |
| 277 | (C2H5, Cl-phenyl-O-C(CH3)2-) | CH3 | —CH2-(tetrahydrofuran-2-yl) | O | $n_D^{20}$ 1.5087 |

*The $^1$H-NMR spectra were recorded in deuterochloroform (CDCl$_3$) using tetramethylsilane (TMS) as the internal standard. The chemical shift is given as the δ value in ppm.

Use Examples

In the following use examples, the compounds shown below were employed as comparison substances:

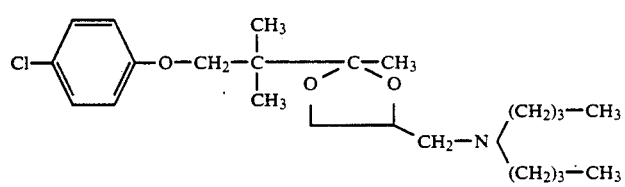

(A)

2-[3-(4-chlorophenoxy)-2-methyl-prop-2-yl]-2-methyl-4-[N,N-di-(n-butyl-aminomethyl]-1,3-dioxolane

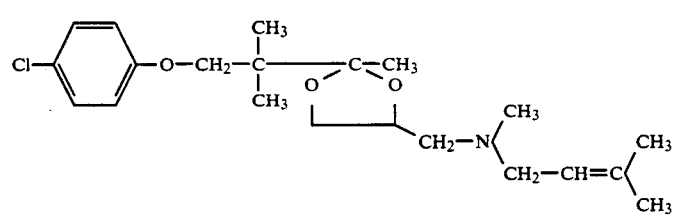

(B)

2-[3-(4-chlorophenoxy)-2-methyl-prop-2-yl]-2-methyl-4-[N-methyl-N-(3-methylbut-2-en-1-yl)-aminomethyl]-1,3-dioxolane

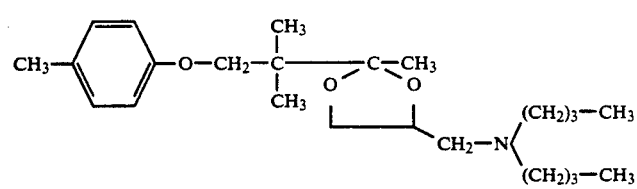

(C)

2-[3-(4-methylphenoxy)-2-methyl-prop-2-yl]-2-methyl-4-[N,N-di-(n-butyl)-aminomethyl]-1,3-dioxolane (known from EP 97,822)

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate

Example A

Pyricularia test (rice)/systemic is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 55, 56, 57 and 86.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

TABLE A

Pyricularia test (rice)/systemic

| Active compound | Application rate in mg of active compound per 100 cm$^2$ | Disease infestation in % of the untreated control |
|---|---|---|
| 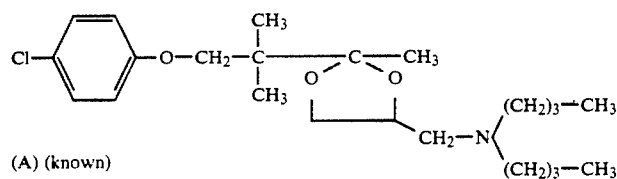 (A) (known) | 100 | 100 |
| 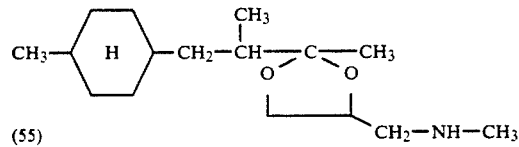 (55) | 100 | 20 |
| 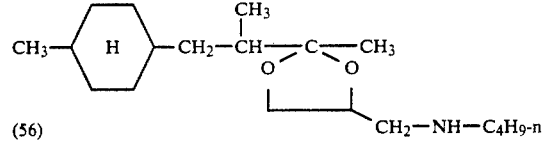 (56) | 100 | 20 |
| 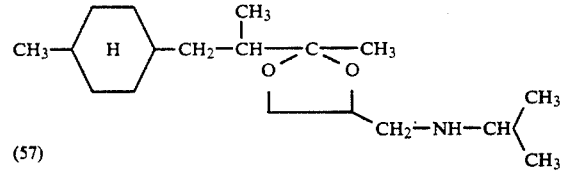 (57) | 100 | 20 |
| 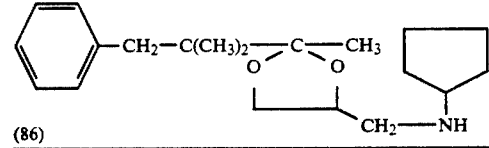 (86) | 100 | 20 |

Example B

Venturia test (apple)/protective
Solvent: 4.7 parts by weight of acetone
Emulsifier: 0.3 parts by weight of alkylaryl polyglycol ether In this test, a clearly superior activity compared with the prior art is shown, for example, by the compounds according to the following preparation examples: 2, 58, 62, 63, 64, 65, 67, 72, 73, 76, 112, 118, 122, 123, 127 and 128.

TABLE B

Venturia test (apple)/protective

| Active compound | Infestation in % at an active compound concentration of 10 ppm |
|---|---|
| (B) (known) 4-Cl-C$_6$H$_4$-O-CH$_2$-C(CH$_3$)$_2$-[dioxolane with CH$_3$]-CH$_2$-N(CH$_3$)-CH$_2$-CH=C(CH$_3$)$_2$ | 63 |
| (58) C$_6$H$_5$-CH$_2$-C(CH$_3$)$_2$-[dioxolane with CH$_3$]-CH$_2$-NH-CH$_3$ | 16 |
| (62) C$_6$H$_5$-CH$_2$-C(CH$_3$)$_2$-[dioxolane with CH$_3$]-CH$_2$-NH-C$_4$H$_9$-n | 9 |
| (63) 3-CH$_3$-C$_6$H$_4$-CH$_2$-C(CH$_3$)$_2$-[dioxolane with CH$_3$]-CH$_2$-NH-CH$_2$-CH(CH$_3$)$_2$ | 11 |
| (64) 3-CH$_3$-C$_6$H$_4$-CH$_2$-C(CH$_3$)$_2$-[dioxolane with CH$_3$]-CH$_2$-NH-C$_2$H$_5$ | 6 |
| (65) 3-CH$_3$-C$_6$H$_4$-CH$_2$-C(CH$_3$)$_2$-[dioxolane with CH$_3$]-CH$_2$-NH-C$_3$H$_7$-n | 25 |
| (67) 3-CH$_3$-C$_6$H$_4$-CH$_2$-C(CH$_3$)$_2$-[dioxolane with CH$_3$]-CH$_2$-NH-C$_4$H$_9$-n | 25 |
| (72) 3-CH$_3$-cyclohexyl-CH$_2$-C(CH$_3$)$_2$-[dioxolane with CH$_3$]-CH$_2$-NH-C$_3$H$_7$-n | 28 |

TABLE B-continued

| Active compound | Venturia test (apple)/protective Infestation in % at an active compound concentration of 10 ppm |
|---|---|
| (73) cyclohexyl-CH₃ with CH₂—C(CH₃)₂—C(CH₃)(O-O)—CH₂—NH—C₄H₉-n | 23 |
| (76) 4-Cl-C₆H₄—CH₂—C(CH₃)₂—C(CH₃)(O-O)—CH₂—NH—C₄H₉-n | 25 |
| (112) Cl₃-C₆H₄—CH(O-O)—CH₂—NH—CH₃ | 20 |
| (118) 3-methylcyclohexyl—CH₂—C(CH₃)₂—C(CH₃)(O-O)—CH₂—NH—cyclopentyl | 16 |
| (2) 3-methylcyclohexyl—CH₂—C(CH₃)₂—C(CH₃)(O-O)—CH₂—NH—cyclohexyl | 9 |
| (122) cyclohexyl—CH₂—C(CH₃)₂—C(CH₃)(O-O)—CH₂—NH—cyclohexyl | 14 |
| (123) cyclohexyl—CH₂—C(CH₃)₂—C(CH₃)(O-O)—CH₂—NH—cyclopentyl | 40 |
| (127) 2-methylcyclohexyl—CH₂—C(CH₃)₂—C(CH₃)(O-O)—CH₂—NH—CH₂—CH(CH₃)₂ | 23 |

TABLE B-continued

Venturia test (apple)/protective

| Active compound | Infestation in % at an active compound concentration of 10 ppm |
|---|---|
| (128) Structure: cyclohexyl(CH3)-CH2-C(CH3)2-C(CH3)(O-CH2-CH(CH2-NH-C4H9-n)-O) dioxolane | 9 |

Example C

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples: 7, 78, 122, 123, 125, 127, 128, 129, 134, 136, 138, 141, 142, 144, 145, 151, 154, 155, 156, 173 and 179.

TABLE C

Erysiphe test (barley)/protective

| Active compound | Active compound concentration in the spray liquor in % by weight | Disease infestation in % of the untreated control |
|---|---|---|
| (A) (known) 4-Cl-C6H4-O-CH2-C(CH3)2-dioxolane-CH2-N((CH2)3-CH3)2 | 0.0025 | 83.8 |
| (C) (known) 4-CH3-C6H4-O-CH2-C(CH3)2-dioxolane-CH2-N((CH2)3-CH3)2 | 0.0025 | 100 |
| (B) (known) 4-Cl-C6H4-O-CH2-C(CH3)2-dioxolane-CH2-N(CH3)(CH2-CH=C(CH3)2) | 0.0025 | 100 |

TABLE C-continued

Erysiphe test (barley)/protective

| Active compound | Active compound concentration in the spray liquor in % by weight | Disease infestation in % of the untreated control |
|---|---|---|
| (78) 3-methylcyclohexyl-CH$_2$-C(CH$_3$)$_2$-[dioxolane with C-CH$_3$]-CH$_2$-NH-CH$_3$ | 0.0025 | 12.5 |
| (173) 4-tert-butylcyclohexyl-CH$_2$-CH(CH$_3$)-[dioxolane with C-H]-CH$_2$-NH-C(CH$_3$)$_3$ | 0.0025 | 27.4 |
| (179) 3-chloro-4-trifluoromethoxyphenyl-[dioxolane with C-H]-CH$_2$-NH-C$_6$H$_{13}$-n | 0.0025 | 25.0 |
| (2) 3-methylcyclohexyl-CH$_2$-C(CH$_3$)$_2$-[dioxolane with C-CH$_3$]-CH$_2$-NH-cyclohexyl | 0.0025 | 21.2 |
| (122) cyclohexyl-CH$_2$-C(CH$_3$)$_2$-[dioxolane with C-CH$_3$]-CH$_2$-NH-cyclohexyl | 0.0025 | 12.5 |
| (123) cyclohexyl-CH$_2$-C(CH$_3$)$_2$-[dioxolane with C-CH$_3$]-CH$_2$-NH-cyclopentyl | 0.0025 | 12.5 |
| (125) 2-methylphenyl-CH$_2$-C(CH$_3$)$_2$-[dioxolane with C-CH$_3$]-CH$_2$-NH-C$_4$H$_9$-n | 0.0025 | 21.2 |

TABLE C-continued
Erysiphe test (barley)/protective
| Active compound | Active compound concentration in the spray liquor in % by weight | Disease infestation in % of the untreated control |
|---|---|---|
| (127) 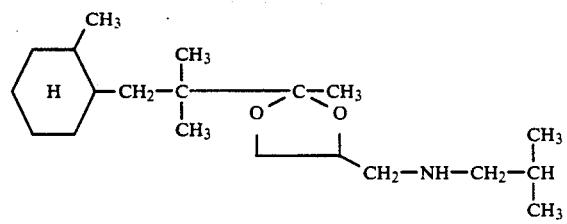 | 0.0025 | 0.0 |
| (128) 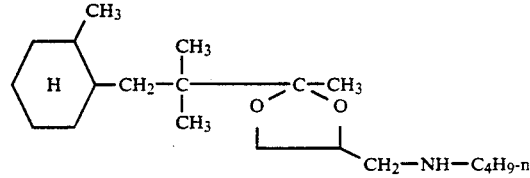 | 0.0025 | 0.0 |
| (129) 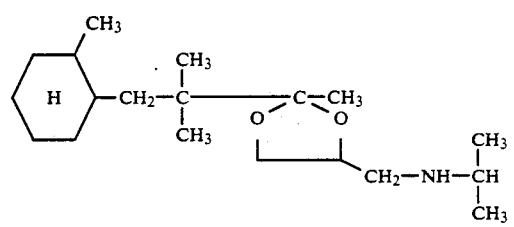 | 0.0025 | 0.0 |
| (134) 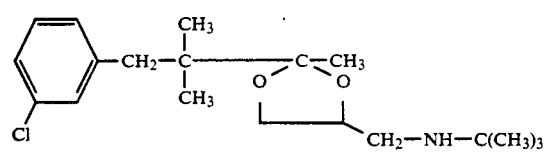 | 0.0025 | 12.5 |
| (136) 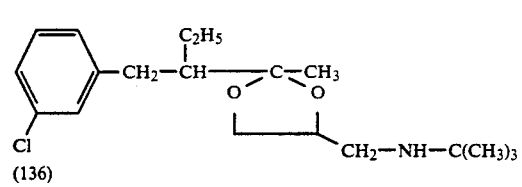 | 0.0025 | 21.2 |
| (138) 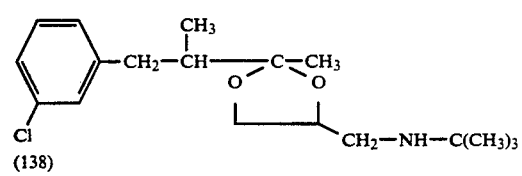 | 0.025 | 25.0 |
| (141) 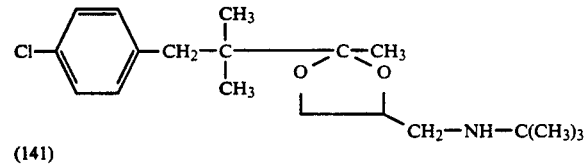 | 0.0025 | 16.2 |

TABLE C-continued

Erysiphe test (barley)/protective

| Active compound | Active compound concentration in the spray liquor in % by weight | Disease infestation in % of the untreated control |
|---|---|---|
| 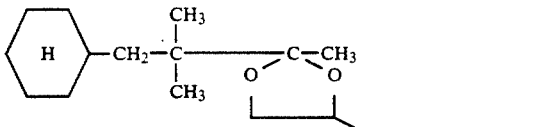 (142) | 0.0025 | 0.0 |
| 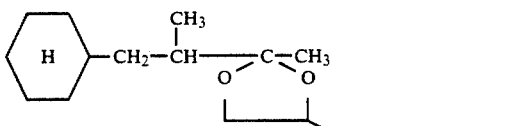 (144) | 0.0025 | 21.2 |
| 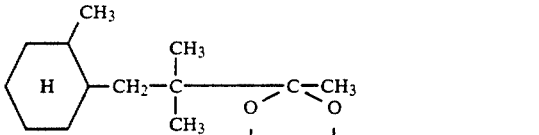 (145) | 0.0025 | 12.5 |
| 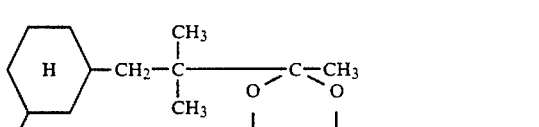 (151) | 0.0025 | 3.7 |
| 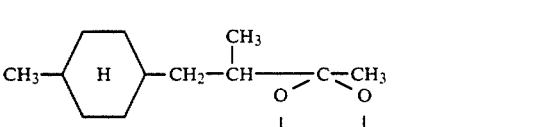 (154) | 0.0025 | 12.5 |
| 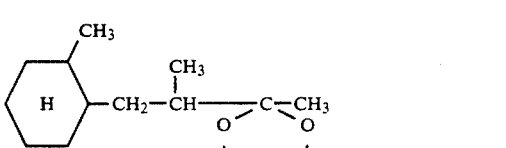 (155) | 0.0025 | 0.0 |
| 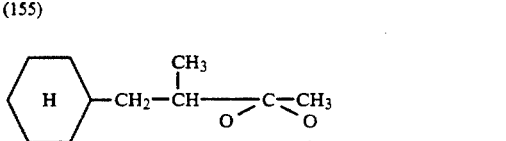 (156) | 0.0025 | 12.5 |

It will be appreciated that the instant specification and claims are set forth by way of illustration and not limitation, and that various modifications and changes may be made without departing from the spirit and scope of the present invention.

What is claimed is:

1. A substituted aminomethylheterocyclic compound or salt of the formula

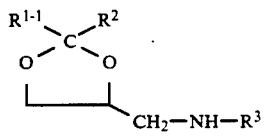 (Ia)

in which
R$^{1-1}$ represents monosubstituted to polysubstituted phenyl, the substituents being identical or different, or optionally monosubstituted to polysubstituted naphthyl, the substituents being identical or different and said substituents being in each case halogen, cyano, nitro, in each case straight-chain or branched alkyl, alkoxy, alkylthio, halogenoalkyl, halogenoalkoxy, halogenoalkylthio in each case having 1 to 6 carbon atoms and which may be further substituted with 1 to 9 identical or different halogen atoms, cyclohexyl or phenyl; in addition represents in each case optionally monosubstituted to polysubstituted cycloalkyl or cycloalkenyl in each case having 5 to 7 carbon atoms, tetrahydronaphthyl or decahydronaphthyl, the substituents being identical or different and said substituents being in each case straight-chain or branched alkyl, halogenoalkyl or halogenoalkoxy in each case having 1 to 6 carbon atoms and which may be further substituted with 1 to 9 identical or different halogen atoms; in addition represents an

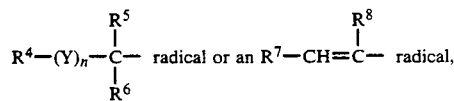

where
R$^4$ represents in each case optionally monosubstituted, disubstituted or trisubstituted cyclohexyl, cyclohexenyl or phenyl, the substituents being identical or different and possible cyclohexyl or cyclohexenyl substituents being in each case straight-chain or branched alkyl, alkoxy or halogenoalkyl in each case having 1 to 4 carbon atoms and which may be further substituted with 1 to 9 halogen atoms, and said phenyl substituents being halogen, cyano, nitro, in each case straight-chain or branched alkyl, alkoxy, alkylthio, halogenoalkyl, halogenoalkoxy or halogenoalkylthio in each case having 1 to 4 carbon atoms and which may be further substituted with 1 to 9 identical or different halogen atoms, cyclohexyl or phenyl,
Y represents oxygen, sulphur, a —CH$_2$— group, an —O—CH$_2$— group, an —S—CH$_2$— group, a sulphinyl group, a sulphonyl group, an

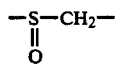

group or an —SO$_2$—CH$_2$— group,
n represents a number 0 or 1,
R$^5$ represents hydrogen, methyl or ethyl,
R$^6$ represents hydrogen or methyl,
R$^7$ represents optionally monosubstituted, disubstituted or trisubstituted phenyl, the substituents being identical or different and said phenyl substituents being those mentioned in the case of R$^4$, and
R$^8$ represents methyl or ethyl,
R$^2$ represents hydrogen or methyl, and
R$^3$ represents in each case straight-chain or branched alkyl having 1 to 12 carbon atoms, alkenyl having 3 to 8 carbon atoms, alkynyl having 3 to 8 carbon atoms, hydroxyalkyl having 2 to 6 carbon atoms, alkoxyalkyl or dialkoxyalkyl in each case having 1 to 6 carbon atoms or hydroxyalkoxyalkyl having 2 to 6 carbon atoms in the individual alkyl parts, or cycloalkyl or cycloalkylalkyl in each case having 3 to 7 carbon atoms in the cycloalkyl part and which may be further substituted with 1 to 4 carbon atoms in the alkyl part and each of which is optionally monosubstituted to polysubstituted in the cycloalkyl part, the substituents being identical or different and said substituents being in each case halogen and in each case straight-chain or branched alkyl, alkoxy, halogenoalkyl or halogenoalkoxy in each case having 1 to 4 carbon atoms, and which may be further substituted with 1 to 9 identical or different halogen atoms; in addition represents aryl, arylalkyl or arylalkenyl in each case having 6 to 10 carbon atoms in the aryl part and, if appropriate, up to 6 carbon atoms in each straight-chain or branched alkyl or alkenyl part and each of which is optionally monosubstituted or polysubstituted in the aryl part by identical or different substituents, said aryl substituents being in each case halogen, cyano, nitro and in each case straight-chain or branched alkyl, alkoxy, alkylthio, halogenoalkyl, halogenoalkoxy, halogenoalkylthio, alkoxycarbonyl or alkoximinoalkyl in each case having 1 to 4 carbon atoms in the individual alkyl parts and which may be further substituted with 1 to 9 identical or different halogen atoms, or represents in each case straight-chain or branched furanylalkyl, tetrahydrofuranylalkyl, tetrahydropyranylalkyl, dioxolanylalkyl or dioxanylalkyl in each case having 1 to 4 carbon atoms in the alkyl part.

2. A substituted aminomethylheterocyclic compound or salt according to claim 1, in which
R$^{1-1}$ represents monosubstituted, disubstituted or trisubstituted phenyl, the substituents being identical or different, or optionally monosubstituted, disubstituted or trisubstituted naphthyl, the substituents being identical or different and possible substituents being in each case fluorine, chlorine, bromine, methyl, i-propyl, t-butyl, trifluoromethyl, trifluoromethoxy, trifluoromethylthio, methoxy, phenyl or cyclohexyl; in addition represents in each case optionally monosubstituted, disubstituted or trisubstituted cyclohexyl, cyclohexenyl, tetrahydronaphthyl or decahydronaphthyl, the substituents being identical or different and possible substituents being in each case straight-chain or branched alkyl having 1 to 4 carbon atoms; in addition represents

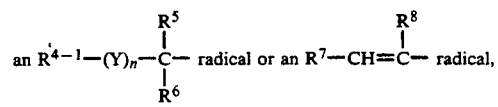

where
R$^4$ represents cyclohexyl or cyclohexenyl, each of which is optionally monosubstituted, disubstituted or trisubstituted by methyl, i-propyl, t-butyl, methoxy, propoxy, butoxy or trifluoromethyl, the substituents being identical or different, or represents phenyl which is optionally monosubstituted, disubstituted or trisubstituted by fluorine, chlorine, bromine, methyl, i-propyl, t-butyl, trifluoromethyl, trifluoromethoxy, trifluoromethylthio, methoxy, phenyl or cyclohexyl, the substituents being identical or different, Y represents oxygen, sulphur, a —$CH_2$— group, an —O—$CH_2$— group or an —S—$CH_2$— group, n represents a number 0 or 1, $R^6$ represents hydrogen or methyl, and $R^7$ represents phenyl which is optionally monosubstituted, disubstituted or trisubstituted by fluorine, chlorine, methyl, isopropyl, t-butyl, trifluoromethyl, trifluoromethoxy, trifluoromethylthio, methoxy, phenyl or cyclohexyl, the substituents being identical or different, and $R^8$ represents methyl or ethyl, $R^2$ represents hydrogen or methyl, $R^3$ represents methyl, ethyl, n- or i-propyl, n-, i-, s- or t-butyl, n- or i-pentyl, n- or i-hexyl, n- or i-heptyl, n- or i-octyl, allyl, n- or i-butenyl, n- or i-pentenyl, propargyl, n- or i-butinyl, hydroxyethyl, hydroxypropyl, methoxyethyl, ethoxyethyl, propoxyethyl, butoxyethyl, methoxypropyl, ethoxypropyl, propoxypropyl, butoxypropyl, hydroxyethoxyethyl, dimethoxyethyl, dimethoxypropyl, diethoxyethyl, represents cyclopropyl, cyclopropylmethyl, cyclopropylethyl, cyclopropylpropyl, cyclopentyl, cyclopentylmethyl, cyclohexyl or cyclohexylmethyl, each of which is optionally monosubstituted to pentasubstituted by fluorine, chlorine, bromine, methyl, ethyl, n- or i-propyl, n-, i-, s- and/or t-butyl, the substituents being identical or different, or represents in each case optionally monosubstituted, disubstituted or trisubstituted phenyl, benzyl or phenylethyl, the substituents being identical or different and possible substituents being in each case fluorine, chlorine, bromine, cyano, nitro, methyl, ethyl, n- or i-propyl.

3. A compound according to claim 1, wherein such compound is 4-n-pentylaminomethyl-2-methyl-2-(4-chlorobenzyl)-1,3-dioxalane of the formula

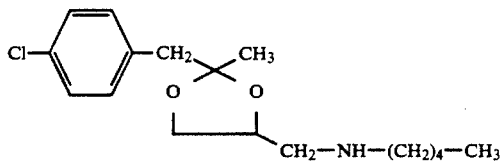

or an acid addition salt thereof.

4. A compound according to claim 1, wherein such compound is 4-n-hexylaminomethyl-2-methyl-2-(4-chlorobenzyl)-1,3-dioxalane of the formula

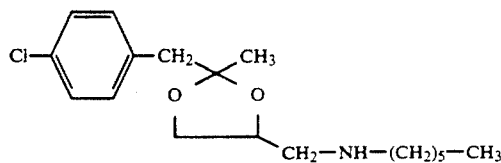

or an acid addition salt thereof.

5. A compound according to claim 1, wherein such compound is 4-ethylaminomethyl-2-[1-(4-chlorophenyl)-2-methyl-prop-2-yl]-1,3-dioxalane of the formula

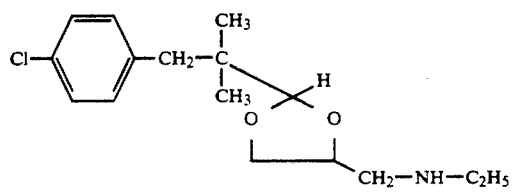

or an acid addition salt thereof.

6. A compound according to claim 1, wherein such compound is 4-n-butylaminomethyl-2-[1-(4-chlorophenyl)-2-methyl-prop-2-yl]-1,3-dioxalane of the formula

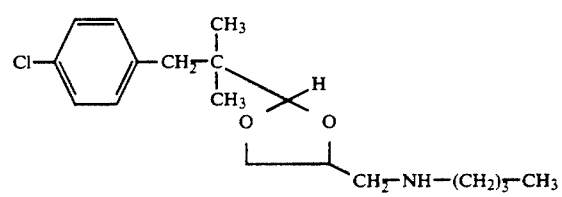

or an acid addition salt thereof.

7. A compound according to claim 1, wherein such compound is 4-cyclopentylaminomethyl-2-[1-(4-chlorophenyl)-2-methyl-prop-2-yl]-1,3-dioxalane of the formula

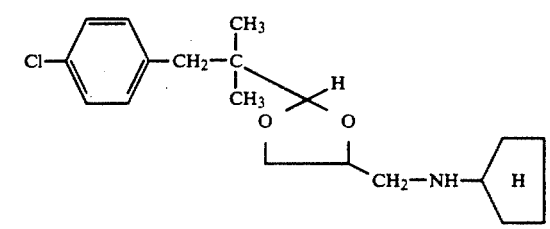

or an acid addition salt thereof.

8. A compound according to claim 1, wherein such compound is 4-n-propylaminomethyl-2-[1-(2,4-dichlorophenoxy)-2-methyl-prop-2-yl]-1,3-dioxalane of the formula

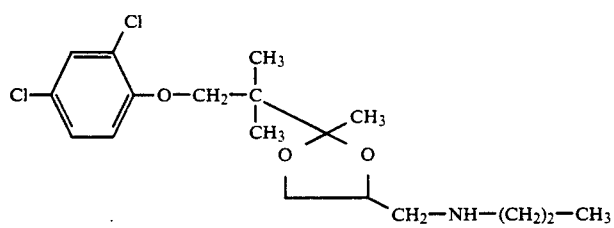
or an acid addition salt thereof.
9. A fungicidal or bactericidal composition comprising a fungicidally or bactericidally effective amount of a compound or salt according to claim 1 and a diluent.
* * * * *

UNITED STATES PATENT AND TRADEMARK OFFICE
CERTIFICATE OF CORRECTION

PATENT NO. : 5,128,368

DATED : July 7, 1992

INVENTOR(S) : Kramer, et al.

It is certified that error appears in the above-identified patent and that said Letters Patent is hereby corrected as shown below:

Title Page      ABSTRACT: Line delete " pt, 10 " and substitute

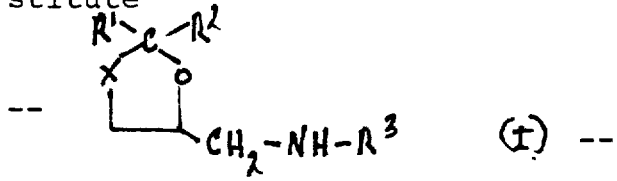

Col. 90, line 61    Delete " 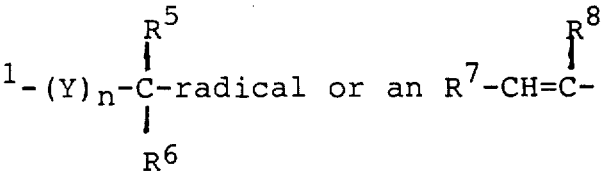 "

and substitute

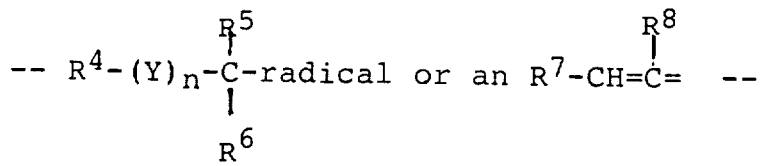

UNITED STATES PATENT AND TRADEMARK OFFICE
CERTIFICATE OF CORRECTION

PATENT NO. : 5,128,368
DATED : July 7, 1992
INVENTOR(S) : Wolfgang Kramer, et al It is certified that error appears in the above-indentified patent and that said Letters Patent is hereby corrected as shown below:

Col. 91, line 44   Delete " ca$e " and substitute -- case --

Signed and Sealed this

Twenty-second Day of March, 1994

Attest:

BRUCE LEHMAN

*Attesting Officer*    *Commissioner of Patents and Trademarks*